(12) United States Patent
Yerkes et al.

(10) Patent No.: US 8,841,233 B2
(45) Date of Patent: Sep. 23, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND 4-HYDROXYPHENYL-PYRUVATE DIOXYGENASE (HPPD) INHIBITORS

(71) Applicant: Dow AgroSciences LLC, Indianapolis, IN (US)

(72) Inventors: Carla N. Yerkes, Crawfordsville, IN (US); Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/833,372

(22) Filed: Mar. 15, 2013

(65) Prior Publication Data
US 2014/0031212 A1 Jan. 30, 2014

Related U.S. Application Data

(60) Provisional application No. 61/675,063, filed on Jul. 24, 2012.

(51) Int. Cl.
| | | |
|---|---|---|
| *A01N 25/26* | (2006.01) | |
| *A01N 43/40* | (2006.01) | |
| *A01N 43/56* | (2006.01) | |
| *A01N 41/10* | (2006.01) | |
| *A01N 43/80* | (2006.01) | |

(52) U.S. Cl.
CPC ............... *A01N 43/80* (2013.01); *A01N 43/40* (2013.01); *A01N 43/56* (2013.01); *A01N 41/10* (2013.01)
USPC .......................................... 504/100; 504/130

(58) Field of Classification Search
CPC ..................................................... A01N 43/40
See application file for complete search history.

(56) References Cited

U.S. PATENT DOCUMENTS

| | | | |
|---|---|---|---|
| 7,314,849 B2 * | 1/2008 | Balko et al. ............ | 504/244 |
| 7,622,641 B2 * | 11/2009 | McCutchen et al. .......... | 800/300 |
| 2009/0062121 A1 | 3/2009 | Satchivi et al. | |
| 2010/0137137 A1 | 6/2010 | Rosinger et al. | |
| 2011/0082162 A1 * | 4/2011 | Lorsbach et al. ............ | 514/274 |
| 2011/0207607 A1 * | 8/2011 | Satchivi et al. ............ | 504/105 |
| 2012/0115727 A1 | 5/2012 | Satchivi et al. | |
| 2012/0190551 A1 * | 7/2012 | Yerkes et al. ............ | 504/242 |
| 2013/0109569 A1 | 5/2013 | Dave | |
| 2013/0310256 A1 * | 11/2013 | Yerkes et al. ............ | 504/103 |
| 2014/0031210 A1 * | 1/2014 | Yerkes et al. ............ | 504/103 |
| 2014/0031211 A1 * | 1/2014 | Yerkes et al. ............ | 504/103 |
| 2014/0031213 A1 * | 1/2014 | Yerkes et al. ............ | 504/103 |
| 2014/0031214 A1 * | 1/2014 | Yerkes et al. ............ | 504/103 |
| 2014/0031215 A1 * | 1/2014 | Yerkes et al. ............ | 504/103 |
| 2014/0031216 A1 * | 1/2014 | Yerkes et al. ............ | 504/103 |
| 2014/0031217 A1 * | 1/2014 | Yerkes et al. ............ | 504/103 |
| 2014/0031218 A1 * | 1/2014 | Mann et al. ............ | 504/103 |
| 2014/0031219 A1 * | 1/2014 | Yerkes et al. ............ | 504/103 |
| 2014/0031220 A1 * | 1/2014 | Yerkes et al. ............ | 504/103 |
| 2014/0031221 A1 * | 1/2014 | Yerkes et al. ............ | 504/103 |
| 2014/0031222 A1 * | 1/2014 | Yerkes et al. ............ | 504/103 |
| 2014/0031227 A1 * | 1/2014 | Yerkes et al. ............ | 504/128 |
| 2014/0031228 A1 * | 1/2014 | Mann et al. ............ | 504/130 |
| 2014/0031229 A1 * | 1/2014 | Mann et al. ............ | 504/136 |

FOREIGN PATENT DOCUMENTS

WO    WO-2007082098    *    7/2007

OTHER PUBLICATIONS

Synthesis of Esters: Esterification Reactions, obtained via google.com in U.S. Appl. No. 13/840,306, obtained online Mar. 8, 2014.*
Steglich Esterification, Organic Chemistry Portal in U.S. Appl. No. 13/840,306.*
Chui, M.P., Non-Final Office Action in U.S. Appl. No. 13/840,306, Mar. 13, 2014, pp. 1-12, USPTO.*
Pryor, A.N., Notice of Allowance and Fee(s) Due for U.S. Appl. No. 13/832,978, Apr. 9, 2014, pp. 1-13, USPTO.*

(Continued)

*Primary Examiner* — Alton Pryor
(74) *Attorney, Agent, or Firm* — Faegre Baker Daniels LLP

(57) ABSTRACT

Provided herein are synergistic herbicidal compositions containing and methods of controlling undesirable vegetation utilizing (a) a compound of formula (I):

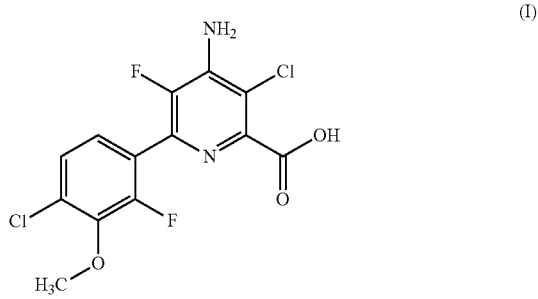

(I)

or an agriculturally acceptable salt or ester thereof and (b) HPPD inhibitors e.g., benzobicyclon, benzofenap, isoxaflutole, mesotrione, pyrazolynate, sulcotrione, and tefuryltrione, or a salt or ester thereof. The compositions and methods provided herein provide control of undesirable vegetation, e.g., in direct-seeded rice, water-seeded rice, transplanted rice, cereals, wheat, barley, oats, rye, sorghum, corn or maize, sugarcane, sunflower, oilseed rape, canola, sugar beet, soybean, cotton, pineapple, vegetables, pastures, grasslands, rangelands, fallowland, turf, tree and vine orchards, plantation crops, aquatics or industrial vegetation management (IVM) or rights-of-way (ROW).

18 Claims, No Drawings

(56) References Cited

OTHER PUBLICATIONS

Pryor, A.N., Notice of Allowance and Fee(s) Due for U.S. Appl. No. 13/833,315, Jun. 25, 2014, pp. 1-2, USPTO.*
Pryor, A.N., Notice of Allowance and Fee(s) Due for U.S. Appl. No. 13/833,315, May 12, 2014, pp. 1-8, USPTO.*
Pryor, A.N., Notice of Allowance and Fee(s) Due for U.S. Appl. No. 13/833,315, Mar. 20, 2014, pp. 1-11, USPTO.*
Pryor, A.N., Notice of Allowance and Fee(s) Due for U.S. Appl. No. 13/833,362, May 29, 2014, pp. 1-8, USPTO.*
Pryor, A.N., Notice of Allowance and Fee(s) Due for U.S. Appl. No. 13/833,659, Mar. 17, 2014, pp. 1-12, USPTO.*
Pryor, A.N., Notice of Allowance and Fee(s) Due for U.S. Appl. No. 13/840,488, May 2, 2014, pp. 1-8, USPTO.*
Pryor, A.N., Notice of Allowance and Fee(s) Due for U.S. Appl. No. 13/833,965, Apr. 1, 2014, pp. 1-8, USPTO.*
Pryor, A.N., Notice of Allowance and Fee(s) Due for U.S. Appl. No. 13/834,326, May 13, 2014, pp. 1-4, USPTO.*
Pryor, A.N., Notice of Allowance and Fee(s) Due for U.S. Appl. No. 13/834,326, Apr. 2, 2014, pp. 1-9, USPTO.*
Pryor, A.N., Notice of Allowance and Fee(s) Due for U.S. Appl. No. 13/836,653, Apr. 2, 2014, pp. 1-8, USPTO.*
Pryor, A.N., Notice of Allowance and Fee(s) Due for U.S. Appl. No. 13/836,653, Jun. 17, 2014, pp. 1-5, USPTO.*
Pryor, A.N., Notice of Allowance and Fee(s) Due for U.S. Appl. No. 13/836,653, Jul. 16, 2014, pp. 1-5, USPTO.*
Pryor, A.N., Notice of Allowance and Fee(s) Due for U.S. Appl. No. 13/837,990, Apr. 1, 2014, pp. 1-8, USPTO.*
Pryor, A.N., Notice of Allowance and Fee(s) Due for U.S. Appl. No. 13/839,043, May 27, 2014, pp. 1-5, USPTO.*
Pryor, A.N., Notice of Allowance and Fee(s) Due for U.S. Appl. No. 13/839,043, Mar. 24, 2014, pp. 1-8, USPTO.*
Pryor, A.N., Notice of Allowance and Fee(s) Due for U.S. Appl. No. 13/839,043, Jun. 27, 2014, pp. 1-2, USPTO.*
Pryor, A.N., Notice of Allowance and Fee(s) Due for U.S. Appl. No. 13/840,303, Apr. 25, 2014, pp. 1-8, USPTO.*
Pryor, A.N., Notice of Allowance and Fee(s) Due for U.S. Appl. No. 13/834,706, Mar. 12, 2014, pp. 1-13, USPTO.*
Pryor, A.N., Notice of Allowance and Fee(s) Due for U.S. Appl. No. 13/834,706, Jul. 9, 2014, pp. 1-7, USPTO.*
Pryor, A.N., Notice of Allowance and Fee(s) Due for U.S. Appl. No. 13/833,923, May 2, 2014, pp. 1-9, USPTO.*
Pryor, A.N., Notice of Allowance and Fee(s) Due for U.S. Appl. No. 13/840,419, May 5, 2014, pp. 1-8, USPTO.*
Pryor, A.N., Notice of Allowance and Fee(s) Due for U.S. Appl. No. 13/840,419, Jun. 25, 12, 2014, pp. 1-2, USPTO.*
Pryor, A.N., Notice of Allowance and Fee(s) Due for U.S. Appl. No. 13/840,236, Apr. 25, 2014, pp. 1-8, USPTO.*
Pryor, A.N., Notice of Allowance and Fee(s) Due for U.S. Appl. No. 13/840,346, Jun. 4, 2014, pp. 1-8, USPTO.*
Thomas, S., Written Opinion of the International Search Authority for PCT/US2013/051325, Dec. 5, 2013, pp. 1-5, ISA/US.
Thomas, S., International Search Report for PCT/US2013/051325, Dec. 5, 2013, pp. 1-4, ISA/US.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND 4-HYDROXYPHENYL-PYRUVATE DIOXYGENASE (HPPD) INHIBITORS

PRIORITY CLAIM

This application claims the benefit of U.S. provisional patent application No. 61/675,063 filed on Jul. 24, 2012, this provisional application is incorporated herein by reference in its entirety.

FIELD

Provided herein are herbicidal compositions comprising (a) 4-amino-3-chloro-5-fluoro-6-(4-chloro-2-fluoro-3-methoxyphenyl)pyridine-2-carboxylic acid or an agriculturally acceptable ester or salt thereof and (b) a 4-hydroxyphenyl-pyruvate dioxygenase (HPPD) inhibitor, as well as methods of controlling undesirable vegetation comprising applying (a) and (b).

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment of the invention provided herein includes herbicidal compositions comprising an herbicidally effective amount of (a) a compound of the formula (I)

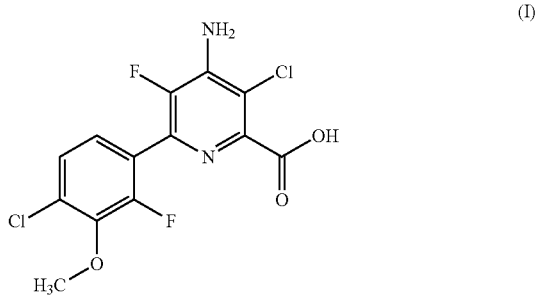 [SMILES: COc1c(Cl)ccc(-c2nc(C(=O)O)c(Cl)c(N)c2F)c1F]

(I)

or an agriculturally acceptable salt or ester thereof, and (b) at least one HPPD inhibitor.

A second embodiment includes the mixture of the first embodiment in which of formula (I), is present in the form of at least one of the following forms: a carboxylic acid, a carboxylate salt, an aralkyl, an alkyl ester, an unsubstituted benzyl, a substituted benzyl, a $C_{1-4}$ alkyl, and/or an n-butyl ester.

A third embodiment includes the mixture according to either the first or second embodiments wherein the (b) at least one HPPD inhibitor is at least one compound selected from the group consisting of: mesotrione, sulcotrione, pyrazolynate, benzobicyclon, isoxaflutole, benzofenap, and tefuryltrione, or an agriculturally acceptable salt, carboxylic acid, carboxylate salt, or ester thereof of at least one of the aforementioned HPPD inhibitor.

A fourth embodiment includes the mixtures according to any of the first, second, or third embodiments in which the HPPD inhibitor in the mixture is benzobicyclon wherein the weight ratio of the compound of formula (I) to benzobicyclon given in units of gae/ha to gai/ha or gae/ha to gae/ha is selected from the group of ranges of ratios and ratios consisting of about 1:150 to 6:1, 1:9.43, 1:472, 1:18.9, 1:9.4, 1:38, 1:19, 1:37.7 to 1:4.7, 1:11.4, 1:5.7, 1:23, 1:11.4, 1:46, 1:23, 1:4.7 to 1:5.7, 1:23, 1:46, 1:46 to 1:11, 1:19, 1:19 to 1:4.7, 1:2.6, 1.18, and 1:23 to 1:6, or within any range defined between any pair of the foregoing values.

A fifth embodiment includes the mixtures according to any of the first, second, or third embodiments in which the HPPD inhibitor in the mixture is benzofenap wherein the weight ratio of the compound of formula (I) to benzofenap given in units of gae/ha to gai/ha or gae/ha to gae/ha is selected from the group of ranges of ratios and ratios consisting of about: 1:272 to 1:2, 1:600 to 3:1, 1:300 to 3:1, 1:200 to 3:1, 1:100 to 3:1, 1:100 to 10:1, within any range defined between any pair of the foregoing values.

A sixth embodiment includes the mixtures according to any of the first, second, or third embodiments in which the HPPD inhibitor in the mixture is isoxaflutole wherein the weight ratio of the compound of formula (I) to isoxaflutole given in units of gae/ha to gai/ha or gae/ha to gae/ha is selected from the group of ranges of ratios and ratios consisting of about: 1:70 to 2:1, 1:4.38, 1:2.19, 1:1, 1:4.4 to 1:1 and 1:2, or within any range defined between any pair of the foregoing values.

A seventh embodiment includes the mixtures according to any of the first, second, or third embodiments in which the HPPD inhibitor in the mixture is mesotrione wherein the weight ratio of the compound of formula (I) to mesotrione given in units of gae/ha to gai/ha or gae/ha to gae/ha is selected from the group of ranges of ratios and ratios consisting of about: 1:115 to 17:1, 1:4, 1:2, 1:1, 1:1.7, 1:8, 1:3.3, 1:16, 1:8 to 1:1, 1:1 to 1:16, or within any range defined between any pair of the foregoing values.

An eighth embodiment includes the mixtures according to any of the first, second, or third embodiments in which the HPPD inhibitor in the mixture is pyrazolynate wherein the weight ratio of the compound of formula (I) to pyrazolynate given in units of gae/ha to gai/ha or gae/ha to gae/ha is selected from the group of ranges of ratios and ratios consisting of about: 1:229 to 2:1, 1:4.3, 1:3, 1:8, 1:9, 1:2 to 1:9, 1:4.3 to 1:1, 1:0.4, 1:0.8, 1:1.6, 1:0.4 to 1:1.6, 1:17, 1:4.3 to 1:17.1, 1:8.6 to 1:17, or within any range defined between any pair of the foregoing values.

A ninth embodiment includes the mixtures according to any of the first, second, or third embodiments in which the HPPD inhibitor in the mixture is sulcotrione wherein the weight ratio of the compound of formula (I) to sulcotrione given in units of gae/ha to gai/ha or gae/ha to gae/ha is selected from the group of ranges of ratios and ratios consisting of about: 1:300 to 13:1, 1:9, 1:3, 1:4, 1:17, 1:34, 1:4.3 to 1:34.3, 1:2, 1:5, 1:8.6 to 1:35, or within any range defined between any pair of the foregoing values.

A tenth embodiment includes the mixtures according to any of the first, second, or third embodiments in which the HPPD inhibitor in the mixture is tefuryltrione wherein the weight ratio of the compound of formula (I) to tefuryltrione given in units of gae/ha to gai/ha or gae/ha to gae/ha is selected from the group of ranges of ratios and ratios consisting of about: 1:300 to 6:1, 1:200 to 6.1, 1:100 to 6.1, 1:300 to 1:1, 1:200 to 1.1, 1:100 to 1:1, or within any range defined between any pair of the foregoing values.

An eleventh embodiment includes any composition according to any of the first through the tenth embodiments wherein the mixture further comprises at least one an agriculturally acceptable agent selected from the group consisting of an adjuvant, a carrier, or a safener.

A twelfth embodiment includes methods of controlling undesirable vegetation comprising the step of applying or otherwise contacting vegetation and/or soil, and/or water with a herbicidally effective amount of at least one mixture according to any of the first through the eighth embodiments.

A thirteenth embodiment includes methods according to the twelfth embodiment wherein undesirable vegetation is controlled according to at least technique selected from the group consisting of: direct-seeded, water-seeded, and/or transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM), or rights-of-way (ROW).

A fourteenth embodiment includes methods according to either of the twelfth and thirteenth embodiments wherein a herbicidally effective amount of the mixture is applied either pre- or post-emergently to at least one of the following: a crop, a field, a ROW, or a paddy.

A fifteenth embodiment includes methods according to any of the ninth through the eleventh embodiments wherein the undesirable vegetation controlled by an application of a herbicidally effective amount of the mixture and at least one of the following phytotoxic actives: glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, or bromoxynil-tolerant crops.

A sixteenth embodiment includes a at least one method according to any of the twelfth through the fifteenth embodiments wherein a plant that is tolerant to at least one herbicide is treated, and where the tolerant crop possesses multiple or stacked traits conferring tolerance to multiple herbicides or inhibitors of multiple modes of action, in some embodiments the treated plant that expresses resistance to a herbicide is a itself undesirable vegetation.

A seventeenth embodiment includes methods according to the sixteenth embodiment, wherein the resistant or tolerant weed is a biotype with resistance or tolerance to multiple herbicides, multiple chemical classes, inhibitors of multiple herbicide modes-of-action, or via multiple resistance mechanisms.

An eighteenth embodiment includes at least one of the methods according to either the sixteenth or seventeenth embodiments, wherein the resistant or tolerant undesirable plant is a biotype resistant or tolerant to at least on agent selected from the groups consisting of: acetolactate synthase (ALS) inhibitors or acetohydroxy acid synthase (AHAS), photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

A nineteenth embodiment includes methods of controlling undesirable vegetation comprising the step of applying a herbicidally effective amount of at least one mixture according to the fourth embodiment wherein the amount of the mixture is applied at a rate, expressed in gai/ha or gae/ha of benzobicyclon selected from the group of rates and ranges of rates consisting of, about: 50, 100, 200 or within any range defined between any pair of the foregoing values.

A twentieth embodiment includes methods according to either of the fourth and nineteenth embodiments wherein the controlled plant is at least one plant selected from the group consisting of: SCPJU, ECHCO, CYPIR, CYPRO, ECHOR, ECHCG and SCPMA, still other embodiments include controlling plants from the genera consisting of: *echinochloa, schoenoplectus, cyperus, bolboschoenus.*

An twenty-first embodiment includes methods of controlling undesirable vegetation comprising the step of applying a herbicidally effective amount of at least one a mixture according to the fifth embodiment wherein the amount of the mixture is applied at a rate, expressed in gai/ha or gae/ha of benzofenap selected from the group of rates and ranges of rates consisting of, about: 25, 50, 100, 200, 300, 400, 500, 600, 102 to 650, 100 to 500, 50 to 200, 50 to 100, or within any range defined between any pair of the foregoing values.

A twenty-second embodiment includes methods according to either of the fifth and twenty-first embodiments wherein the controlled plant is at least one plant selected from the group consisting of: ECHCG, still other embodiments include controlling plants from the genera consisting of: *Echinoch loa.*

A twenty-third embodiment includes methods of controlling undesirable vegetation comprising the step of applying a herbicidally effective amount of at least one a mixture according to the sixth embodiment wherein the amount of the mixture is applied at a rate, expressed in gai/ha or gae/ha of isoxaflutole selected from the group of rates and ranges of rates consisting of, about: 10, 25, 35, 70, 100, or within any range defined between any pair of the foregoing values.

A twenty-fourth embodiment includes methods according to either of the sixth and twenty-third embodiments wherein the controlled plant is at least one plant selected from the group consisting of: IPOHE, XANST and SETVI still other embodiments include controlling plants from the genera consisting of: *ipomoea, xanthium* and *setaria.*

A twenty-fifth embodiment includes methods of controlling undesirable vegetation comprising the step of applying a herbicidally effective amount of at least one a mixture according to the seventh embodiment wherein the amount of the mixture is applied at a rate, expressed in gai/ha or gae/ha of mesotrione selected from the group of rates and ranges of rates consisting of, about: 5, 10, 17.5, 35, 70, 100, 140, 200, 280, or within any range defined between any pair of the foregoing values.

A twenty-sixth embodiment includes methods according to either of the seventh and twenty-fifth embodiments wherein the controlled plant is at least one plant selected from the group consisting of: BRAPP, ECHCO, CYPIR, IPOHE, SCPJU, DIGSA, ECHCG, ECHOR, FLMMI and SCAMPA, still other embodiments include controlling plants from the genera consisting of: *brachiaria, echinochloa, cyperus, ipomoea, schoenoplectus, digitaria, fibrisyyles* and *bolboschoenus*.

A twenty-seventh embodiment includes methods of controlling undesirable vegetation comprising the step of applying a herbicidally effective amount of at least one a mixture according to the eighth embodiment wherein the amount of the mixture is applied at a rate, expressed in gai/ha or gae/ha of pyrazolynate selected from the group of rates and ranges of rates consisting of, about: 10, 25, 37.5, 70, 100 and 150, or within any range defined between any pair of the foregoing values.

A twenty-eighth embodiment includes methods according to either of the ninth and twenty-seventh embodiments wherein the controlled plant is at least one plant selected from the group consisting of: ECHCG, ECHCO, LEFCH, FLMMI, SCPMA, ECHOR, and CYPRO, still other embodiments include controlling plants from the genera consisting of: *echinochloa, leptochloa, fimbristylis, bolboxhoenuis* and *cyperus*.

A twenty-ninth embodiment includes methods of controlling undesirable vegetation comprising the step of applying a herbicidally effective amount of at least one a mixture according to the ninth embodiment wherein the amount of the mixture is applied at a rate, expressed in gai/ha or gae/ha of sulcotrione selected from the group of rates and ranges of rates consisting of, about: 10, 20, 37.5, 70, 100, 150, 200, 250 and 300, or within any range defined between any pair of the foregoing values.

A thirtieth embodiment includes methods according to either of the ninth and twenty-seventy-ninth embodiments wherein the controlled plant is at least one plant selected from the group consisting of: BRAPP, DIGSA, EZHCG, and IPOHE, still other embodiments include controlling plants from the genera consisting of: *brachiara, urochloa, digitaria, echinochloa*, and *ipomoea*.

Provided herein are herbicidal compositions comprising a herbicidally effective amount of (a) a compound of the formula (I)

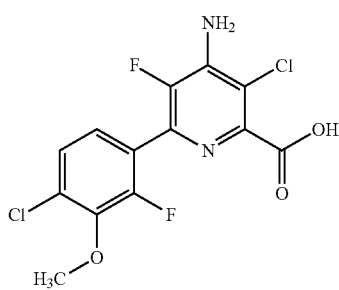

or an agriculturally acceptable salt or ester of thereof, and (b) a synthetic auxin herbicide. The compositions may also contain an agriculturally acceptable adjuvant or carrier.

Provided herein are also methods of controlling undesirable vegetation comprising applying (a) a compound of formula (I) or an agriculturally acceptable ester or salt thereof and (b) a synthetic auxin herbicide or an agriculturally acceptable salt or ester thereof.

DETAILED DESCRIPTION

Definitions

As used herein, the compound of formula (I) has the following structure:

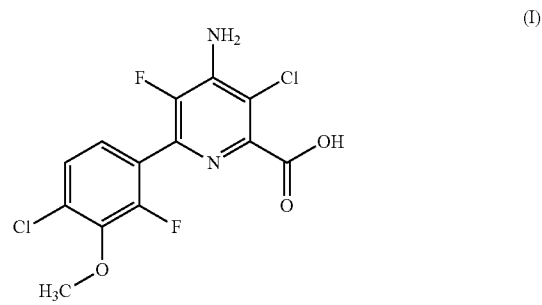 [SMILES: COc1c(Cl)ccc(-c2nc(C(=O)O)c(Cl)c(N)c2F)c1F]

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Without being limited to any theory, HPPD inhibitors are inhibitors of 4-hydroxyphenylpyruvate dioxygenase, an oxygenase involved in the creation of energy in plants and higher order eukaryotes. Exemplary HPPD inhibitors include, but are not limited to, benzobicyclon, benzofenap, isoxaflutole, mesotrione, pyrazolynate, sulcotrione, and tefuryltrione.

As used herein, benzobicyclon is 3-(2-chloro-4-mesylbenzoyl)-2-phenylthiobicyclo[3.2.1]oct-2-en-4-one. Exemplary uses of benzobicyclon are described in Tomlin, C., ed. A World Compendium The Pesticide Manual. 15th ed. Alton: BCPC Publications, 2009 (hereafter "*The Pesticide Manual*, Fifteenth Edition, 2009."). Exemplary uses of benzobicyclon include its use for pre-emergent and post-emergence control of annual and perennial paddy weeds in direct-seeded and transplanted rice. Benzobicyclon possesses the following structure:

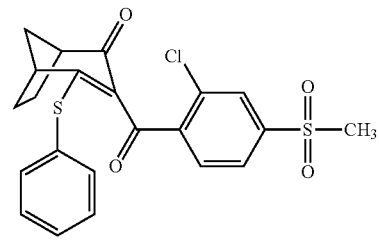 [SMILES: CS(=O)(=O)c1ccc(C(=O)C2=C(Sc3ccccc3)C3CCC(C3)C2=O)c(Cl)c1]

As used herein, benzofenap is 2-{[4-(2,4-dichloro-3-methylbenzoyl)-1,3-dimethyl-1H-pyrazol-5-yl]oxy}-1-(4-methylphenyl)ethan-1-one. Its herbicidal activity is exemplified in *The Pesticide Manual*, Fifteenth Edition, 2009. Benzofenap provides pre-emergence control of annual and perennial broad-leaf weeds in rice, primarily being used in transplanted rice where it is absorbed through the roots and bases of target weeds. Benzofenap possesses the following structure:

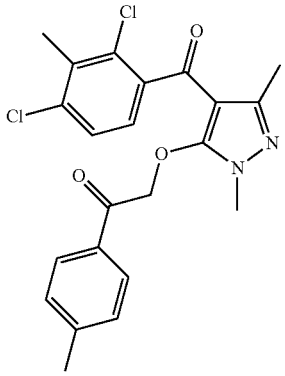 [SMILES: Cc1ccc(C(=O)COc2c(C(=O)c3ccc(Cl)c(C)c3Cl)c(C)nn2C)cc1]

As used herein, isoxaflutole is (5-cyclopropyl-4-isoxazolyl)[2-(methylsulfonyl)-4-(trifluoromethyl)phenyl]methanone. Exemplary uses of isoxaflutole are described in *The Pesticide Manual*, Fifteenth Edition, 2009. Exemplary uses of isoxaflutole include its use for pre-emergence control of broadleaf weeds and grass weeds in maize. Isoxaflutole possesses the following structure:

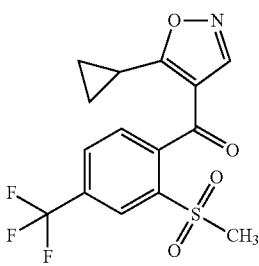 [SMILES: CS(=O)(=O)c1cc(C(F)(F)F)ccc1C(=O)c1cnoc1C1CC1]

As used herein, mesotrione is 2-[4-(methylsulfonyl)-2-nitrobenzoyl]-1,3-cyclohexanedione. Exemplary uses of mesotrione are provided in *The Pesticide Manual*, Fifteenth Edition, 2009. Exemplary uses of mesotrione include its use for pre-emergence and post-emergence control of broadleaf weeds and grass weeds in maize. Mesotrione possesses the following structure:

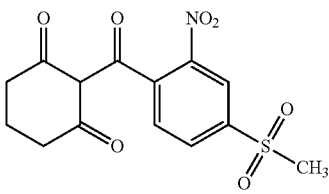 [SMILES: CS(=O)(=O)c1ccc(C(=O)C2C(=O)CCCC2=O)c([N+](=O)[O-])c1]

As used herein, pyrazolynate is (2,4-dichlorophenyl)[1,3-dimethyl-5-[[(4-methylphenyl)sulfonyl]oxy]-1H-pyrazol-4-yl]methanone. Exemplary uses of pyrazolynate are described in *The Pesticide Manual*, Fifteenth Edition, 2009. Exemplary uses of pyrazolynate include its use for control of grasses, sedges, *Potamogeton distinctus, Sagittaria pygmaea, Sagittaria trifolia* and *Alisma canaliculatum* in paddy rice. Pyrazolynate possesses the following structure:

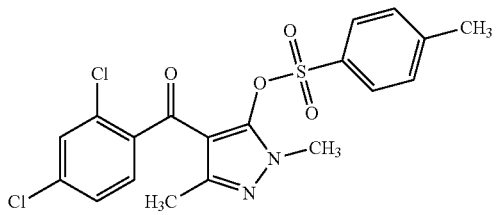 [SMILES: Cc1ccc(S(=O)(=O)Oc2c(C(=O)c3ccc(Cl)cc3Cl)c(C)nn2C)cc1]

As used herein, sulcotrione is 2-[2-chloro-4-(methylsulfonyl)benzoyl]-1,3-cyclohexanedione. Exemplary uses of sulcotrione are described in *The Pesticide Manual*, Fifteenth Edition, 2009. Exemplary uses of sulcotrione include its use for control of broadleaf weeds and grasses post-emergence in maize and sugar cane. Sulcotrione possesses the following structure:

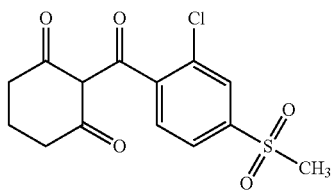 [SMILES: CS(=O)(=O)c1ccc(C(=O)C2C(=O)CCCC2=O)c(Cl)c1]

As used herein, tefuryltrione is 2-{2-chloro-4-mesyl-3-[(RS)-tetrahydro-2-furylmethoxymethyl]benzoyl}cyclohexane-1,3-dione. Its herbicidal activity is exemplified in *The Pesticide Manual*, Fifteenth Edition, 2009. Tefuryltrione provides control of broadleaf and sedge weeds in rice. Tefuryltrione possesses the following structure:

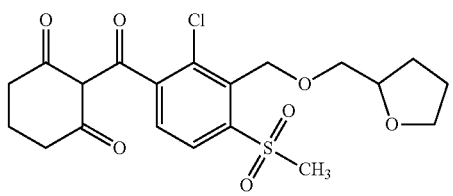 [SMILES: CS(=O)(=O)c1ccc(C(=O)C2C(=O)CCCC2=O)c(Cl)c1COCC1CCCO1]

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

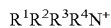

$R^1R^2R^3R^4N^+$ wherein $R^1$, $R^2$, $R^3$ and $R^4$ each, independently, represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

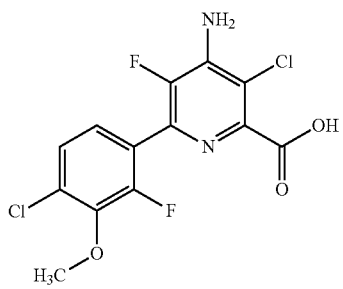

(I)

or an agriculturally acceptable salt or ester of thereof, and (b) an HPPD inhibitor.

Provided herein are also methods of controlling undesirable vegetation comprising contacting the vegetation or the locus thereof, i.e., area adjacent to the plant, with or applying to the soil or water to prevent the emergence or growth of vegetation a herbicidally effective amount of the compound of formula (I) or agriculturally acceptable salt or ester thereof and (b) an HPPD inhibitor. In certain embodiments, the methods employ the compositions described herein.

In certain embodiments, of the compositions and methods provided herein, the HPPD inhibitor is, including, but not limited to, benzobicyclon, benzofenap, isoxaflutole, mesotrione, pyrazolynate, sulcotrione, or tefuryltrione, and all salts and esters thereof.

Furthermore, in some embodiments, the combination of compound (I) or agriculturally acceptable salt or ester thereof and an HPPD inhibitor, or an agriculturally acceptable salt or ester thereof exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. 9$^{th}$ ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and one of benzobicyclon, mesotrione, pyrazolynate and sulcotrione, or an agriculturally acceptable salt or ester thereof, are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, plantation crops, vegetables, aquatics, industrial vegetation management (IVM) and rights-of-way (ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation in glyphosate-tolerant-, 5-enolpyruvylshikimate-3-phosphate (EP SP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, plantation crops, vegetables, aquatics, industrial vegetation management (IVM) and rights of way ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schult. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Pres') Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* POIR. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus ret-*

*roflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Eleusine indica* (L.) Gaertn. (goosegrass, ELEIN), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (kyllinga, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Brachiaria* or *Urochloa, Cyperus, Digitaria, Echinochloa, Fimbristylis, Ipomoea, Leptochloa, Schoenoplectus/Bolboschoenus, Setaria*, and *Xanthium*.

In some embodiments, the combination of compound (I) or agriculturally acceptable ester or salt thereof and benzobicyclon, mesotrione, pyrazolynate, sulcotrione, and tefuryltrione, or agriculturally acceptable salt or ester thereof is used to control broadleaf signalgrass (*Brachiaria platyphylla* (Griseb.) Nash or *Urochloa platyphylla* (Nash) R. D. Webster, BRAPP), yellow nutsedge, (*Cyperus esculentus* L., CYPES), purple nutsedge (*Cyperus rotundus* L., CYPRO), rice flatsedge (*Cyperus iria* L., CYPIR), large crabgrass (*Digitaria sanguinalis* (L.) Scop., DIGSA), barnyardgrass (*Echinochloa* crus-galli (L.) Beauv., ECHCG), junglerice (*Echinochloa colona* (L.) Link, ECHCO), early watergrass (*Echinochloa oryzoides* (Ard.) Fritsch, ECHOR), globe fringerush (*Fimbristylis miliacea* (L.) Vahl, FIMMI), ivyleaf morningglory (*Ipomoea hederacea* Jacq., IPOHE), Chinese sprangletop (*Leptochloa chinensis* (L.) Nees, LEFCH), Japanese bulrush (*Schoenoplectus juncoides* (Roxb.) Palla, SCPJU), sea clubrush (*Bolboschoenus maritimus* (L.) Palla or *Schoenoplectus maritimus* (L.) Lye, SCPMA), green foxtail (*Setaria viridis* (L.) Beauv., SETVI), and common cocklebur (*Xanthium strumarium* L.).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In some embodiments, an agriculturally acceptable ester or salt of compound (I) is employed. In certain embodiments, an agriculturally acceptable ester is employed. In certain embodiments, the ester is a $C_{1-4}$ alkyl ester. In certain embodiments, the ester is an n-butyl ester. In certain embodiments, the ester is a benzyl ester. In certain embodiments, compound (I), which is a carboxylic acid, is employed.

In certain embodiments of the compositions and methods described herein, the compound of formula (I) or salt or ester thereof is used in combination with benzobicyclon. With regard to the compositions, in some embodiments, the weight ratio of the compound of formula (I) or salt or ester thereof to benzobicyclon is within the range of from about 1:150 to about 6:1. In certain embodiments, the weight ratio of the compound of formula (I) or salt or ester thereof to benzobicyclon is within the range of from 1:45 to about 2.5:1. In certain embodiments, the weight ratio of the compound of formula (I) or salt or ester thereof to benzobicyclon is within the range of from about 1:80 to about 1:2. In certain embodiments, the weight ratio of the compound of formula (I) or salt or ester thereof to benzobicyclon is within the range of from about 1:40 to about 1:5. In certain embodiments, the compositions provided herein comprise the compound of formula (I) or its benzyl ester and benzobicyclon. In one embodiment, the composition comprises the compound of formula (I) and benzobicyclon, wherein the weight ratio of the compound of formula (I) to benzobicyclon is about 1:40 to about 1:5. In one embodiment, the composition comprises the benzyl ester of the compound of formula (I) and benzobicyclon, wherein the weight ratio of the benzyl ester of the compound of formula (I) to benzobicyclon is about 1:40 to about 1:5.7. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 600 gai/ha based on the total amount of active ingredients in the composition. In certain embodiments, the composition is applied at an application rate of from about 54 gai/ha to about 240 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and benzobicyclon, e.g., sequentially or simultaneously. In some embodiments, the benzobicyclon is applied at a rate from about 50 gai/ha to about 300 gai/ha and the compound of formula (I) of salt or ester thereof is applied at a rate from about 2 gae/ha to about 300 gae/ha. In some embodiments, the benzobicyclon is applied at a rate from about 25 gai/ha to about 400 gai/ha and the compound of formula (I) of salt or ester thereof is applied at a rate from about 2 g acid equivalent per hectare (gae/ha) to about 45 gae/ha. In some embodiments, the benzobicyclon is applied at a rate from about 50 gai/ha to about 200 gai/ha and the compound of formula (I) of salt or ester thereof is applied at a rate from about 4.38 g acid equivalent per hectare (gae/ha) to about 21.2 gae/ha. In certain embodiments, the methods utilize the compound of formula (I), or its benzyl ester and benzobicyclon. In one embodiment, the methods utilize the compound of formula (I) and benzobicyclon, wherein the compound of formula (I) is applied at a rate of from about 5.3 g acid equivalent per hectare (gae/ha) to about 21.2 gae/ha, and benzobicyclon is applied at a rate of about 50 gai/ha to about 200 gai/ha. In one embodiment, the methods utilize the benzyl ester of the compound of formula (I) and benzobicyclon, wherein the benzyl ester of the compound of formula (I) is applied at a rate of from about 4.38 g acid equivalent per hectare (gae/ha) to about 17.5 gae/ha, and benzobicyclon is applied at a rate of about 100 gai/ha to about 200 gai/ha. In certain embodiments, the methods and compositions utilizing the compound of formula (I) or salt or ester thereof in combination with benzobicyclon are used to control ECHCG, ECHCO, ECHOR, SCPMA, SCPJU, CYPIR, or CYPRO.

In certain embodiments of the compositions and methods described herein, the compound of formula (I) or salt or ester thereof is used in combination with benzobicyclon. With regard to the compositions, in some embodiments, the weight ratio of the compound of formula (I) or salt or ester thereof to benzobicyclon is within the range of from about 1:150 to about 6:1. In certain embodiments, the weight ratio of the compound of formula (I) or salt or ester thereof to benzobicyclon is within the range of from 1:45 to about 2.5:1. In certain embodiments, the weight ratio of the compound of formula (I) or salt or ester thereof to benzobicyclon is within the range of from about 1:80 to about 1:2. In certain embodiments, the weight ratio of the compound of formula (I) or salt or ester thereof to benzobicyclon is within the range of from about 1:46 to about 2:1. In certain embodiments, the weight ratio of the compound of formula (I) or salt or ester thereof to benzobicyclon is within the range of from about 1:40 to about 1:5. In certain embodiments, the compositions provided herein comprise the compound of formula (I) or its benzyl ester and benzobicyclon. In one embodiment, the composition comprises the compound of formula (I) and benzobicyclon, wherein the weight ratio of the compound of formula (I) to benzobicyclon is about 1:40 to about 1:5. In one embodiment, the composition comprises the benzyl ester of the compound of formula (I) and benzobicyclon, wherein the weight ratio of the benzyl ester of the compound of formula (I) to benzobicyclon is about 1:40 to about 1:5.7. In one embodiment, the composition comprises the benzyl ester of the compound of formula (I) and benzobicyclon, wherein the weight ratio of the benzyl ester of the compound of formula (I) to benzobicyclon is about 1:46 to about 2:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 600 gai/ha based on the total amount of active ingredients in the composition. In certain embodiments, the composition is applied at an application rate of from about 54 gai/ha to about 240 gai/ha based on the total amount of active ingredients in the composition. In certain embodiments, the composition is applied at an application rate of from about 54 gai/ha to about 296 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and benzobicyclon, e.g., sequentially or simultaneously. In some embodiments, the benzobicyclon is applied at a rate from about 50 gai/ha to about 300 gai/ha and the compound of formula (I) of salt or ester thereof is applied at a rate from about 2 gae/ha to about 300 gae/ha. In some embodiments, the benzobicyclon is applied at a rate from about 25 gai/ha to about 400 gai/ha and the compound of formula (I) of salt or ester thereof is applied at a rate from about 2 g acid equivalent per hectare (gae/ha) to about 45 gae/ha. In some embodiments, the benzobicyclon is applied at a rate from about 50 gai/ha to about 200 gai/ha and the compound of formula (I) of salt or ester thereof is applied at a rate from about 4.38 g acid equivalent per hectare (gae/ha) to about 21.2 gae/ha. In some embodiments, the benzobicyclon is applied at a rate from about 50 gai/ha to about 200 gai/ha and the compound of formula (I) of salt or ester thereof is applied at a rate from about 4.38 g acid equivalent per hectare (gae/ha) to about 96 gae/ha. In certain embodiments, the methods utilize the compound of formula (I), or its benzyl ester and benzobicyclon. In one embodiment, the methods utilize the compound of formula (I) and benzobicyclon, wherein the compound of formula (I) is applied at a rate of from about 5.3 g acid equivalent per hectare (gae/ha) to about 21.2 gae/ha, and benzobicyclon is applied at a rate of about 50 gai/ha to about 200 gai/ha. In one embodiment, the methods utilize the compound of formula (I) and benzobicyclon, wherein the compound of formula (I) is applied at a rate of from about 5.3 g acid equivalent per hectare (gae/ha) to about 96 gae/ha, and benzobicyclon is applied at a rate of about 50 gai/ha to about 200 gai/ha. In one embodiment, the methods utilize the benzyl ester of the compound of formula (I) and benzobicyclon, wherein the benzyl ester of the compound of formula (I) is applied at a rate of from about 4.38 g acid equivalent per hectare (gae/ha) to about 17.5 gae/ha, and benzobicyclon is applied at a rate of about 100 gai/ha to about 200 gai/ha. In one embodiment, the methods utilize the benzyl ester of the compound of formula (I) and benzobicyclon, wherein the benzyl ester of the compound of formula (I) is applied at a rate of from about 4.38 g acid equivalent per hectare (gae/ha) to about 96 gae/ha, and benzobicyclon is applied at a rate of about 50 gai/ha to about 200 gai/ha. In certain embodiments, the methods and compositions utilizing the compound of formula (I) or salt or ester thereof in combination with benzobicyclon are used to control ECHCG, ECHCO, ECHOR, SCPMA, SCPJU, CYPIR, or CYPRO.

In certain embodiments of the compositions and methods described herein, the compound of formula (I) or salt or ester thereof is used in combination with benzofenap or salt or ester thereof. In some embodiments, the weight ratio of the compound of formula (I) or salt or ester thereof to benzofenap or salt or ester thereof is within the range of from about 1:600 to about 3:1. In certain embodiments, the weight ratio of the compound of formula (I) or salt or ester thereof to benzofenap or salt or ester thereof is within the range of from 1:272 to about 1:2. The application rate will depend upon the particular type of weed to be controlled, the degree of control required, and the timing and method of application. In some embodiments, the composition is applied at an application rate of from about 100 grams active ingredient per hectare (gai/ha) to about 1500 gai/ha based on the total amount of active ingredients in the composition. In certain embodiments, the composition is applied at an application rate of from about 102 gai/ha to about 650 gai/ha based on the total amount of active ingredients in the composition. In some embodiments, the benzofenap or salt or ester thereof is applied at a rate from about 100 gai/ha to about 1200 gai/ha and the compound of formula (I) of salt or ester thereof is applied at a rate from about 2 gae/ha to about 300 gae/ha.

In certain embodiments of the compositions and methods described herein, the compound of formula (I) or salt or ester thereof is used in combination with isoxaflutole or salt or ester thereof. With regard to the compositions, in some embodiments, the weight ratio of the compound of formula (I) or salt or ester thereof to isoxaflutole or salt or ester thereof is within the range of from about 1:70 to about 12:1. In certain embodiments, the weight ratio of the compound of formula (I) or salt or ester thereof to isoxaflutole or salt or ester thereof is within the range of from 1:23 to about 2:1. In certain embodiments, the compositions comprise the compound of formula (I) or its benzyl or n-butyl ester and isoxaflutole. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 grams active ingredient per hectare (gai/ha) to about 440 gai/ha based on the total amount of active ingredients in the composition. In certain embodiments, the composition is applied at an application rate of from about 29 gai/ha to about 150 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and isoxaflutole, e.g., sequentially or simultaneously. In some embodiments, the isoxaflutole or salt or ester thereof is applied at a rate from about 25 gai/ha to about 140 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and isoxaflutole. In certain embodiments, the methods and compositions utilizing the compound of formula (I) or salt or ester thereof in combination with isoxaflutole are used to control IPOHE, SETVI, or XANST.

In certain embodiments of the compositions and methods described herein, the compound of formula (I) or salt or ester thereof is used in combination with isoxaflutole or salt or ester thereof. With regard to the compositions, in some embodiments, the weight ratio of the compound of formula (I) or salt or ester thereof to isoxaflutole or salt or ester thereof is within the range of from about 1:70 to about 12:1. In certain embodiments, the weight ratio of the compound of formula (I) or salt or ester thereof to isoxaflutole or salt or ester thereof is within the range of from 1:23 to about 2:1. In certain embodiments, the weight ratio of the compound of formula (I) or salt or ester thereof to isoxaflutole or salt or ester thereof is within the range of from 1:9 to about 1:1. In certain embodiments, the compositions comprise the compound of formula (I) or its benzyl or n-butyl ester and isoxaflutole. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 grams active ingredient per hectare (gai/ha) to about 440 gai/ha based on the total amount of active ingredients in the composition. In certain embodiments, the composition is applied at an application rate of from about 29 gai/ha to about 150 gai/ha based on the total amount of active ingredients in the composition. In certain embodiments, the composition is applied at an application rate of from about 43 gai/ha to about 102 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and isoxaflutole, e.g., sequentially or simultaneously. In some embodiments, the isoxaflutole or salt or ester thereof is applied at a rate from about 25 gai/ha to about 140 gai/ha and the compound of formula (I) of salt or ester thereof is applied at a rate from about 2 gae/ha to about 300 gae/ha. In some embodiments, the isoxaflutole or salt or ester thereof is applied at a rate from about 35 gai/ha to about 70 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and isoxaflutole. In certain embodiments, the methods and compositions utilizing the compound of formula (I) or salt or ester thereof in combination with isoxaflutole are used to control IPOHE, SETVI, or XANST.

In certain embodiments of the compositions and methods described herein, the compound of formula (I) or salt or ester thereof is used in combination with mesotrione. With regard to the compositions, in some embodiments, the weight ratio of the compound of formula (I) or salt or ester thereof to mesotrione is within the range of from about 1:115 to about 17:1. In certain embodiments, the weight ratio of the compound of formula (I) or salt or ester thereof to mesotrione is within the range of from 1:32 to about 5:1. In certain embodiments, the weight ratio of the compound of formula (I) or salt or ester thereof to mesotrione is within the range of from about 1:32 to about 2:1. In certain embodiments, the weight ratio of the compound of formula (I) or salt or ester thereof to mesotrione is within the range of from about 1:16 to about 1:1. In certain embodiments, the compositions provided herein comprise the compound of formula (I) or its benzyl or n-butyl ester and mesotrione. In one embodiment, the composition comprises the compound of formula (I) and mesotrione, wherein the weight ratio of the compound of formula (I) to mesotrione is about 1:16 to about 1:1. In one embodiment, the composition comprises the benzyl ester of the compound of formula (I) and mesotrione, wherein the weight ratio of the benzyl ester of the compound of formula (I) to mesotrione is about 1:8 to about 1:2. In one embodiment, the composition comprises the n-butyl ester of the compound of formula (I) and mesotrione, wherein the weight ratio of the n-butyl ester of the compound of formula (I) to mesotrione is about 1:4 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 22 grams active ingredient per hectare (gai/ha) to about 600 gai/ha based on the total amount of active ingredients in the composition. In certain embodiments, the composition is applied at an application rate of from about 54 gai/ha to about 525 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and mesotrione, e.g., sequentially or simultaneously. In some embodiments, the mesotrione is applied at a rate from about 17.5 gai/ha to about 225 gai/ha and the compound of formula (I) of salt or ester thereof is applied at a rate from about 2 gae/ha to about 300 gae/ha. In some embodiments, the mesotrione is applied at a rate from about 8 gai/ha to about 300 gai/ha and the compound of formula (I) of salt or ester thereof is applied at a rate from about 2 g acid equivalent per hectare (gae/ha) to about 300 gae/ha. In some embodiments, the mesotrione is applied at a rate from about 17.5 gai/ha to about 140 gai/ha and the compound of formula (I) of salt or ester thereof is applied at a rate from about 4.38 g acid equivalent per hectare (gae/ha) to about 140 gae/ha. In certain embodiments, the methods utilize the compound of formula (I), or its benzyl or n-butyl ester and mesotrione. In one embodiment, the methods utilize the compound of formula (I) and mesotrione, wherein the compound of formula (I) is applied at a rate of from about 4.38 g acid equivalent per hectare (gae/ha) to about 84.8 gae/ha, and mesotrione is applied at a rate of about 17.5 gai/ha to about 140 gai/ha. In one embodiment, the methods utilize the benzyl ester of the compound of formula (I) and mesotrione, wherein the benzyl ester of the compound of formula (I) is applied at a rate of from about 4.38 g acid equivalent per hectare (gae/ha) to about 140 gae/ha, and mesotrione is applied at a rate of about 17.5 gai/ha to about 140 gai/ha. In one embodiment, the methods utilize the n-butyl ester of the compound of formula (I) and mesotrione, wherein the n-butyl ester of the compound of formula (I) is applied at a rate of about 35 g acid equivalent per hectare (gae/ha) to about 70 gae/ha, and mesotrione is applied at a rate of about 140 gai/ha. In certain embodiments, the methods and compositions utilizing the compound of formula (I) or salt or ester thereof in combination with mesotrione are used to control BRAPP, ECHCO, CYPIR, IPOHE, SCPJU, DIGSA, ECHCG, or ECHOR.

In certain embodiments of the compositions and methods described herein, the compound of formula (I) or salt or ester thereof is used in combination with pyrazolynate. With regard to the compositions, in some embodiments, the weight ratio of the compound of formula (I) or salt or ester thereof to pyrazolynate is within the range of from about 1:229 to about 2:1. In certain embodiments, the weight ratio of the compound of formula (I) or salt or ester thereof to pyrazolynate is within the range of from 1:9 to about 1:4. In certain embodiments, the weight ratio of the compound of formula (I) or salt or ester thereof to pyrazolynate is within the range of from about 1:35 to about 2:1. In certain embodiments, the weight ratio of the compound of formula (I) or salt or ester thereof to pyrazolynate is within the range of from about 1:17.1 to about 1:1. In certain embodiments, the compositions provided herein comprise the compound of formula (I) or its benzyl or n-butyl ester and pyrazolynate. In one embodiment, the composition comprises the compound of formula (I) and pyrazolynate, wherein the weight ratio of the compound of formula (I) to pyrazolynate is about 1:8.6 to about 1:1. In one embodiment, the composition comprises the benzyl ester of the compound of formula (I) and pyrazolynate, wherein the weight ratio of the benzyl ester of the compound of formula (I) to pyrazolynate is about 1:17.1 to about 1:2.1. In one embodiment, the composition comprises the n-butyl ester of the compound of formula (I) and pyrazolynate, wherein the weight ratio of the n-butyl ester of the compound of formula (I) to pyrazolynate is about 1:8.6 to about 1:4.3. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 167 grams active ingredient per hectare (gai/ha) to about 4,300 gai/ha based on the total amount of active ingredients in the composition. In certain embodiments, the composition is applied at an application rate of from about 167 gai/ha to about 200 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyrazolynate, e.g., sequentially or simultaneously. In some embodiments, the pyrazolynate is applied at a rate from about 17.5 gai/ha to about 4,000 gai/ha and the compound of formula (I) of salt or ester thereof is applied at a rate from about 2 gae/ha to about 300 gae/ha. In some embodiments, the pyrazolynate is applied at a rate from about 18 gai/ha to about 300 gai/ha and the compound of formula (I) of salt or ester thereof is applied at a rate of about 2 g acid equivalent per hectare (gae/ha) to about 70 gae/ha. In some embodiments, the pyrazolynate is applied at a rate from about 37.5 gai/ha to about 150 gai/ha and the compound of formula (I) of salt or ester thereof is applied at a rate from about 4.38 g acid equivalent per hectare (gae/ha) to about 35 gae/ha. In certain embodiments, the methods utilize the compound of formula (I), or its benzyl or n-butyl ester and pyrazolynate. In one embodiment, the methods utilize the compound of formula (I) and pyrazolynate, wherein the compound of formula (I) is applied at a rate of from about 8.75 g acid equivalent per hectare (gae/ha) to about 35 gae/ha, and pyrazolynate is applied at a rate of about 37.5 gai/ha to about 150 gai/ha. In one embodiment, the methods utilize the benzyl ester of the compound of formula (I) and pyrazolynate, wherein the benzyl ester of the compound of formula (I) is applied at a rate of from about 4.38 g acid equivalent per hectare (gae/ha) to about 17.5 gae/ha, and pyrazolynate is applied at a rate of about 37.5 gai/ha to about 75 gai/ha. In one embodiment, the methods utilize the n-butyl ester of the compound of formula (I) and pyrazolynate, wherein the n-butyl ester of the compound of formula (I) is applied at a rate of about 17.5 g acid equivalent per hectare (gae/ha) to about 35 gae/ha, and pyrazolynate is applied at a rate of about 150 gai/ha. In certain embodiments, the methods and compositions utilizing the compound of formula (I) or salt or ester thereof in combination with pyrazolynate are used to control LEFCH, IPOHE, ECHCG, ECHCO, ECHOR, FIMMI, SCPMA, CYPRO, or SCPJU.

In certain embodiments of the compositions and methods described herein, the compound of formula (I) or salt or ester thereof is used in combination with pyrazolynate. With regard to the compositions, in some embodiments, the weight ratio of the compound of formula (I) or salt or ester thereof to pyrazolynate is within the range of from about 1:229 to about 2:1. In certain embodiments, the weight ratio of the compound of formula (I) or salt or ester thereof to pyrazolynate is within the range of from 1:9 to about 1:4. In certain embodiments, the weight ratio of the compound of formula (I) or salt or ester thereof to pyrazolynate is within the range of from about 1:35 to about 2:1. In certain embodiments, the weight ratio of the compound of formula (I) or salt or ester thereof to pyrazolynate is within the range of from about 1:17.1 to about 1:1. In certain embodiments, the weight ratio of the compound of formula (I) or salt or ester thereof to pyrazolynate is within the range of from about 1:19 to about 3:1. In certain embodiments, the compositions provided herein comprise the compound of formula (I) or its benzyl or n-butyl ester and pyrazolynate. In one embodiment, the composition comprises the benzyl ester compound of formula (I) and pyrazolynate, wherein the weight ratio of the compound of formula (I) to pyrazolynate is about 1:8.6 to about 1:1. In one embodiment, the composition comprises the benzyl ester of the compound of formula (I) and pyrazolynate, wherein the weight ratio of the benzyl ester of the compound of formula (I) to pyrazolynate is about 1:17.1 to about 1:2.1. In one embodiment, the composition comprises the benzyl ester of the compound of formula (I) and pyrazolynate, wherein the weight ratio of the benzyl ester of the compound of formula (I) to pyrazolynate is about 1:19 to about 3:1. In one embodiment, the composition comprises the n-butyl ester of the compound of formula (I) and pyrazolynate, wherein the weight ratio of the n-butyl ester of the compound of formula (I) to pyrazolynate is about 1:8.6 to about 1:4.3. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 167 grams active ingredient per hectare (gai/ha) to about 4,300 gai/ha based on the total amount of active ingredients in the composition. In certain embodiments, the composition is applied at an application rate of from about 167 gai/ha to about 200 gai/ha based on the total amount of active ingredients in the composition. In certain embodiments, the composition is applied at an application rate of from about 45 gai/ha to about 250 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyrazolynate, e.g., sequentially or simultaneously. In some embodiments, the pyrazolynate is applied at a rate from about 17.5 gai/ha to about 4,000 gai/ha and the compound of formula (I) of salt or ester thereof is applied at a rate from about 2 gae/ha to about 300 gae/ha. In some embodiments, the pyrazolynate is applied at a rate from about 18 gai/ha to about 300 gai/ha and the compound of formula (I) of salt or ester thereof is applied at a rate from about 2 g acid equivalent per hectare (gae/ha) to about 70 gae/ha. In some embodiments, the pyrazolynate is applied at a rate from about 37.5 gai/ha to about 150 gai/ha and the compound of formula (I) of salt or ester thereof is applied at a rate from about 4.38 g acid equivalent per hectare (gae/ha) to about 35 gae/ha. In some embodiments, the pyrazolynate is applied at a rate from about 37.5 gai/ha to about 150 gai/ha and the compound of formula (I) of salt or ester thereof is applied at a rate from about 4.38 g acid equivalent per hectare (gae/ha) to about 96 gae/ha. In certain embodiments, the methods utilize the compound of formula (I), or its benzyl or n-butyl ester and pyrazolynate. In one embodiment, the methods utilize the compound of formula (I) and pyrazolynate, wherein the compound of formula (I) is applied at a rate of from about 8.75 g acid equivalent per hectare (gae/ha) to about 35 gae/ha, and pyrazolynate is applied at a rate of about 37.5 gai/ha to about 150 gai/ha. In one embodiment, the methods utilize the benzyl ester of the compound of formula (I) and pyrazolynate, wherein the benzyl ester of the compound of formula (I) is applied at a rate of from about 4.38 g acid equivalent per hectare (gae/ha) to about 17.5 gae/ha, and pyrazolynate is applied at a rate of about 37.5 gai/ha to about 75 gai/ha. In one embodiment, the methods utilize the benzyl ester of the compound of formula (I) and pyrazolynate, wherein the benzyl ester of the compound of formula (I) is applied at a rate of from about 4.38 g acid equivalent per hectare (gae/ha) to about 96 gae/ha, and pyrazolynate is applied at a rate of about 37.5 gai/ha to about 150 gai/ha. In one embodiment, the methods utilize the n-butyl ester of the compound of formula (I) and pyrazolynate, wherein the n-butyl ester of the compound of formula (I) is applied at a rate of about 17.5 g acid equivalent per hectare (gae/ha) to about 35 gae/ha, and pyrazolynate is applied at a rate of about 150 gai/ha. In certain embodiments, the methods and compositions utilizing the compound of formula (I) or salt or ester thereof in combination with pyrazolynate are used to control LEFCH, IPOHE, ECHCG, ECHCO, ECHOR, FIMMI, SCPMA, CYPRO, or SCPJU.

In certain embodiments of the compositions and methods described herein, the compound of formula (I) or salt or ester thereof is used in combination with sulcotrione. With regard to the compositions, in some embodiments, the weight ratio of the compound of formula (I) or salt or ester thereof to sulcotrione is within the range of from about 1:300 to about 13:1. In certain embodiments, the weight ratio of the compound of formula (I) or salt or ester thereof to sulcotrione is within the range of from 1:34 to about 1:1. In certain embodiments, the weight ratio of the compound of formula (I) or salt or ester thereof to sulcotrione is within the range of from about 1:60 to about 2:1. In certain embodiments, the weight ratio of the compound of formula (I) or salt or ester thereof to sulcotrione is within the range of from about 1:30 to about 1:1.3. In certain embodiments, the compositions provided herein comprise the compound of formula (I) or its benzyl ester and sulcotrione. In one embodiment, the composition comprises the compound of formula (I) and sulcotrione, wherein the weight ratio of the compound of formula (I) to sulcotrione is about 1:30 to about 1:1.3. In one embodiment, the composition comprises the benzyl ester of the compound of formula (I) and sulcotrione, wherein the weight ratio of the benzyl ester of the compound of formula (I) to sulcotrione is about 1:30 to about 1:1.3. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 25 grams active ingredient per hectare (gai/ha) to about 900 gai/ha based on the total amount of active ingredients in the composition. In certain embodiments, the composition is applied at an application rate of from about 27 gai/ha to about 200 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and sulcotrione, e.g., sequentially or simultaneously. In some embodiments, the sulcotrione is applied at a rate from about 5 gai/ha to about 140 gai/ha and the compound of formula (I) of salt or ester thereof is applied at a rate from about 2 gae/ha to about 300 gae/ha. In some embodiments, the sulcotrione is applied at a rate from about 10 gai/ha to about 300 gai/ha and the compound of formula (I) of salt or ester thereof is applied at a rate from about 2 g acid equivalent per hectare (gae/ha) to about 40 gae/ha. In some embodiments, the sulcotrione is applied at a rate from about 22.5 gai/ha to about 150 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and sulcotrione. In one embodiment, the methods utilize the compound of formula (I) and sulcotrione, wherein the compound of formula (I) is applied at a rate of from about 4.38 g acid equivalent per hectare (gae/ha) to about 17.5 gae/ha, and sulcotrione is applied at a rate of about 22.5 gai/ha to about 150 gai/ha. In one embodiment, the methods utilize the benzyl ester of the compound of formula (I) and sulcotrione, wherein the benzyl ester of the compound of formula (I) is applied at a rate of from about 4.38 g acid equivalent per hectare (gae/ha) to about 17.5 gae/ha, and sulcotrione is applied at a rate of about 22.5 gai/ha to about 150 gai/ha. In certain embodiments, the methods and compositions utilizing the compound of formula (I) or salt or ester thereof in combination with sulcotrione are used to control BRAPP, ECHCO, CYPIR, IPOHE, SCPJU, DIGSA, ECHCG, or ECHOR.

In certain embodiments of the compositions and methods described herein, the compound of formula (I) or salt or ester thereof is used in combination with tefuryltrione. With regard to the compositions, in some embodiments, the weight ratio of the compound of formula (I) or salt or ester thereof to tefuryltrione is within the range of from about 1:300 to about 6:1. In certain embodiments, the weight ratio of the compound of formula (I) or salt or ester thereof to tefuryltrione is within the range of from 1:45 to about 1:1. In certain embodiments, the compositions comprise the compound of formula (I) or its benzyl or n-butyl ester and tefuryltrione. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 900 gai/ha based on the total amount of active ingredients in the composition. In certain embodiments, the composition is applied at an application rate of from about 55 gai/ha to about 250 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and tefuryltrione, e.g., sequentially or simultaneously. In some embodiments, tefuryltrione is applied at a rate from about 50 gai/ha to about 600 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and tefuryltrione.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, aciflurofen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, SYN-523, sodium arsenite, sodium azide, sodium chlorate, sulfallate, sulfentrazone, sulfometuron, sulfosate, sulfosulfuron, sulfuric acid, sulglycapin, swep, TCA, tebutam, tebuthiuron, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix. In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenylsulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and an HPPD inhibitor to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 3.0 weight percent active ingredient and in certain embodiments contain about 0.01 to 1.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, and III are greenhouse trial results.

Example I

Evaluation of Post-emergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 h photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)

pyridine-2-carboxylic acid (Compound A), each formulated as an SC (suspension concentrate), and various herbicidal components alone and in combination. Forms of Compound A were applied on an acid equivalent basis.

Forms of compound A (compound of formula I) tested include:

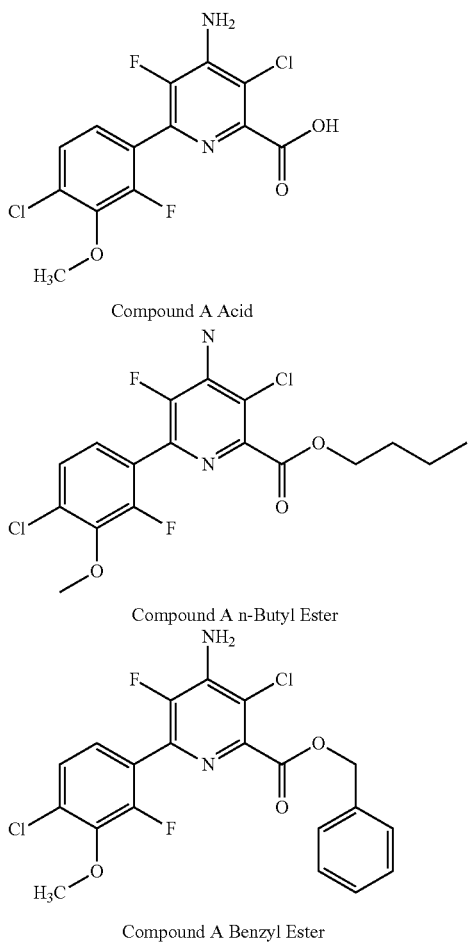

Compound A Acid

Compound A n-Butyl Ester

Compound A Benzyl Ester

Other herbicidal components were applied on an active ingredient basis and included 4-hydroxyphenyl pyruvate dioxygenase (HPPD)-inhibiting herbicides mesotrione formulated as Callisto®, sulcotrione formulated as Mikado®, pyrazolynate formulated as Sunbird® 10% GR, and benzobicyclon formulated as Benzobicyclon 3.5%.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate or water to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m² at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$Expected = A + B - (A \times B/100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-9.

TABLE 1

Synergistic Activity of Foliar-Applied Compound A Acid and Mesotrione Herbicidal Compositions on Weed Control in a Rice Cropping System.

| Compound A Acid | Mesotrione | Visual Weed Control (%) - 20 DAA BRAPP | |
|---|---|---|---|
| gae/ha | gai/ha | Obs | Exp |
| 4.38 | 0 | 60 | — |
| 8.75 | 0 | 60 | — |
| 17.5 | 0 | 85 | — |
| 0 | 17.5 | 0 | — |
| 0 | 35 | 0 | — |
| 4.38 | 17.5 | 80 | 60 |
| 8.75 | 17.5 | 80 | 60 |
| 17.5 | 17.5 | 90 | 85 |
| 4.38 | 35 | 60 | 60 |
| 8.75 | 35 | 80 | 60 |
| 17.5 | 35 | 85 | 85 |

| Compound A Acid | Mesotrione | Visual Weed Control (%) - 20 DAA ECHCO | |
|---|---|---|---|
| gae/ha | gai/ha | Obs | Exp |
| 4.38 | 0 | 40 | — |
| 8.75 | 0 | 60 | — |
| 17.5 | 0 | 85 | — |
| 0 | 17.5 | 0 | — |
| 0 | 35 | 0 | — |
| 0 | 70 | 0 | — |
| 4.38 | 17.5 | 65 | 40 |
| 8.75 | 17.5 | 85 | 60 |
| 17.5 | 17.5 | 80 | 85 |
| 4.38 | 35 | 60 | 40 |
| 8.75 | 35 | 80 | 60 |
| 17.5 | 35 | 95 | 85 |
| 4.38 | 70 | 50 | 40 |
| 8.75 | 70 | 80 | 60 |
| 17.5 | 70 | 95 | 85 |

| Compound A Acid | Mesotrione | Visual Weed Control (%) - 20 DAA CYPIR | |
|---|---|---|---|
| gae/ha | gai/ha | Obs | Exp |
| 4.38 | 0 | 75 | — |
| 8.75 | 0 | 90 | — |
| 17.5 | 0 | 90 | — |
| 0 | 17.5 | 0 | — |
| 0 | 35 | 50 | — |
| 4.38 | 17.5 | 100 | 75 |
| 8.75 | 17.5 | 100 | 90 |
| 17.5 | 17.5 | 100 | 90 |
| 4.38 | 35 | 100 | 88 |
| 8.75 | 35 | 100 | 95 |
| 17.5 | 35 | 100 | 95 |

TABLE 2

Synergistic Activity of Foliar-Applied Compound A Benzyl Ester and Mesotrione Herbicidal Compositions on Weed Control in a Rice Cropping System.

| Compound A Benzyl Ester | Mesotrione | Visual Weed Control (%) - 20 DAA IPOHE | |
|---|---|---|---|
| gae/ha | gai/ha | Obs | Exp |
| 8.75 | 0 | 10 | — |
| 17.5 | 0 | 20 | — |
| 0 | 35 | 25 | — |
| 0 | 70 | 50 | — |
| 8.75 | 35 | 50 | 33 |
| 17.5 | 35 | 40 | 40 |
| 8.75 | 70 | 70 | 55 |
| 17.5 | 70 | 80 | 60 |

| Compound A Benzyl Ester | Mesotrione | Visual Weed Control (%) - 20 DAA SCPJU | |
|---|---|---|---|
| gae/ha | gai/ha | Obs | Exp |
| 4.38 | 0 | 30 | — |
| 8.75 | 0 | 60 | — |
| 0 | 17.5 | 50 | — |
| 0 | 35 | 80 | — |
| 4.38 | 17.5 | 100 | 65 |
| 8.75 | 17.5 | 100 | 80 |
| 4.38 | 35 | 100 | 86 |
| 8.75 | 35 | 100 | 92 |

| Compound A Benzyl Ester | Mesotrione | Visual Weed Control (%) - 20 DAA DIGSA | |
|---|---|---|---|
| gae/ha | gai/ha | Obs | Exp |
| 35 | 0 | 38 | — |
| 0 | 140 | 58 | — |
| 35 | 140 | 88 | 73 |

TABLE 3

Synergistic Activity of Foliar-Applied Compound A Acid and Sulcotrione Herbicidal Compositions on Control of Weeds Common to Rice Cropping Systems.

| Compound A Acid | Sulcotrione | Visual Weed Control (%) - 20 DAA BRAPP | |
|---|---|---|---|
| gae/ha | gai/ha | Obs | Exp |
| 4.38 | 0 | 10 | — |
| 8.75 | 0 | 80 | — |
| 0 | 37.5 | 0 | — |
| 0 | 75 | 20 | — |
| 0 | 150 | 60 | — |
| 4.38 | 37.5 | 65 | 10 |
| 8.75 | 37.5 | 60 | 80 |
| 4.38 | 75 | 55 | 28 |
| 8.75 | 75 | 95 | 84 |
| 4.38 | 150 | 85 | 64 |
| 8.75 | 150 | 100 | 92 |

| Compound A Acid | Sulcotrione | Visual Weed Control (%) - 20 DAA DIGSA | |
|---|---|---|---|
| gae/ha | gai/ha | Obs | Exp |
| 4.38 | 0 | 40 | — |
| 8.75 | 0 | 45 | — |
| 17.5 | 0 | 45 | — |
| 0 | 37.5 | 25 | — |
| 4.38 | 37.5 | 60 | 55 |
| 8.75 | 37.5 | 70 | 59 |
| 17.5 | 37.5 | 75 | 59 |

| Compound A Acid | Sulcotrione | Visual Weed Control (%) - 20 DAA ECHCG | |
|---|---|---|---|
| gae/ha | gai/ha | Obs | Exp |
| 4.38 | 0 | 25 | — |
| 8.75 | 0 | 80 | — |
| 0 | 37.5 | 0 | — |
| 0 | 75 | 20 | — |
| 4.38 | 37.5 | 45 | 25 |
| 8.75 | 37.5 | 90 | 80 |

TABLE 3-continued

Synergistic Activity of Foliar-Applied Compound A Acid and Sulcotrione Herbicidal Compositions on Control of Weeds Common to Rice Cropping Systems.

| 4.38 | 75 | 75 | 40 |
|---|---|---|---|
| 8.75 | 75 | 90 | 84 |

| Compound A Acid | Sulcotrione | Visual Control (%) - 20 DAA IPOHE | |
|---|---|---|---|
| gae/ha | gai/ha | Obs | Exp |
| 4.38 | 0 | 10 | — |
| 8.75 | 0 | 35 | — |
| 17.5 | 0 | 40 | — |
| 0 | 37.5 | 20 | — |
| 4.38 | 37.5 | 50 | 28 |
| 8.75 | 37.5 | 70 | 48 |
| 17.5 | 37.5 | 60 | 52 |

TABLE 4

Synergistic Activity of Foliar-Applied Compound A Benzyl Ester and Sulcotrione Herbicidal Compositions on Control of Weeds Common to Rice Cropping Systems.

| Compound A Benzyl Ester | Sulcotrione | Visual Weed Control (%) - 20 DAA BRAPP | |
|---|---|---|---|
| gae/ha | gai/ha | Obs | Exp |
| 4.38 | 0 | 50 | — |
| 8.75 | 0 | 70 | — |
| 0 | 37.5 | 0 | — |
| 0 | 75 | 20 | — |
| 0 | 150 | 60 | — |
| 4.38 | 37.5 | 80 | 50 |
| 8.75 | 37.5 | 80 | 70 |
| 4.38 | 75 | 75 | 60 |
| 8.75 | 75 | 85 | 76 |
| 4.38 | 150 | 90 | 80 |
| 8.75 | 150 | 90 | 88 |

| Compound A Benzyl Ester | Sulcotrione | Visual Weed Control (%) - 20 DAA DIGSA | |
|---|---|---|---|
| gae/ha | gai/ha | Obs | Exp |
| 4.38 | 0 | 25 | — |
| 8.75 | 0 | 40 | — |
| 17.5 | 0 | 50 | — |
| 0 | 37.5 | 25 | — |
| 4.38 | 37.5 | 70 | 44 |
| 8.75 | 37.5 | 70 | 55 |
| 17.5 | 37.5 | 70 | 63 |

| Compound A Benzyl Ester | Sulcotrione | Visual Weed Control (%) - 20 DAA | | | | | |
|---|---|---|---|---|---|---|---|
| | | ECHCG | | ECHCO | | IPOHE | |
| gae/ha | gai/ha | Obs | Exp | Obs | Exp | Obs | Exp |
| 4.38 | 0 | 40 | — | 40 | — | 10 | — |
| 0 | 37.5 | 0 | — | 15 | — | 20 | — |
| 0 | 75 | 20 | — | 35 | — | 30 | — |
| 0 | 150 | 95 | — | 95 | — | 80 | — |
| 4.38 | 37.5 | 65 | 40 | 75 | 49 | 40 | 28 |
| 4.38 | 75 | 90 | 52 | 80 | 61 | 60 | 37 |
| 4.38 | 150 | 100 | 97 | 100 | 97 | 85 | 82 |

TABLE 5

Synergistic Activity of Foliar-Applied Compound A Acid and Pyrazolynate Herbicidal Compositions on Weed Control in a Rice Cropping System.

| Compound A Acid | Pyrazolynate | Visual Weed Control (%) - 21 DAA | | | |
|---|---|---|---|---|---|
| | | LEFCH | | IPOHE | |
| gae/ha | gai/ha | Obs | Exp | Obs | Exp |
| 17.5 | 0 | 10 | — | 25 | — |
| 35 | 0 | 60 | — | 48 | — |
| 0 | 150 | 5 | — | 10 | — |
| 17.5 | 150 | 40 | 15 | 50 | 33 |
| 35 | 150 | 73 | 62 | 58 | 53 |

TABLE 6

Synergistic Activity of Foliar-Applied Compound A n-Butyl Ester and Pyrazolynate Herbicidal Compositions on Weed Control in a Rice Cropping System.

| Compound A n-Butyl Ester | Pyrazolynate | Visual Weed Control (%) - 21 DAA ECHCG | |
|---|---|---|---|
| gae/ha | gai/ha | Obs | Exp |
| 17.5 | 0 | 78 | — |
| 35 | 0 | 93 | — |
| 0 | 150 | 0 | — |
| 17.5 | 150 | 90 | 78 |
| 35 | 150 | 95 | 93 |

TABLE 7

Synergistic Activity of Foliar-Applied Compound A Benzyl Ester and Pyrazolynate Herbicidal Compositions on Weed Control in a Rice Cropping System.

| Compound A Benzyl Ester | Pyrazolynate | Visual Weed Control (%) - 22 DAA ECHCG | |
|---|---|---|---|
| gae/ha | gai/ha | Obs | Exp |
| 8 | 0 | 35 | — |
| 16 | 0 | 65 | — |
| 32 | 0 | 80 | — |
| 0 | 37.5 | 0 | — |
| 0 | 75 | 0 | — |
| 8 | 37.5 | 40 | 35 |
| 16 | 37.5 | 70 | 65 |
| 32 | 37.5 | 95 | 80 |
| 8 | 75 | 40 | 35 |
| 16 | 75 | 70 | 65 |
| 32 | 75 | 95 | 80 |

TABLE 8

Synergistic Activity of Foliar-Applied Compound A Acid and Benzobicyclon Herbicidal Compositions on Weed Control in a Rice Cropping System.

| Compound A Acid | Benzo-bicyclon | Visual Weed Control (%) - 22 DAA | | | | | |
|---|---|---|---|---|---|---|---|
| | | ECHCG | | ECHCO | | SCPJU | |
| gae/ha | gai/ha | Obs | Exp | Obs | Exp | Obs | Exp |
| 5.3 | 0 | 65 | — | 65 | — | 60 | — |
| 10.6 | 0 | 55 | — | 65 | — | 75 | — |
| 0 | 50 | 0 | — | 10 | — | 50 | — |
| 0 | 100 | 20 | — | 10 | — | 60 | — |
| 0 | 200 | 15 | — | 85 | — | 70 | — |

TABLE 8-continued

Synergistic Activity of Foliar-Applied Compound
A Acid and Benzobicyclon Herbicidal Compositions
on Weed Control in a Rice Cropping System.

| Compound | Benzo- | Visual Weed Control (%) - 22 DAA | | | | | |
|---|---|---|---|---|---|---|---|
| A Acid | bicyclon | ECHCG | | ECHCO | | SCPJU | |
| gae/ha | gai/ha | Obs | Exp | Obs | Exp | Obs | Exp |
| 5.3 | 50 | 65 | 65 | 90 | 69 | 95 | 80 |
| 10.6 | 50 | 85 | 55 | 90 | 69 | 90 | 88 |
| 5.3 | 100 | 80 | 72 | 90 | 69 | 95 | 84 |
| 10.6 | 100 | 85 | 64 | 85 | 69 | 100 | 90 |
| 5.3 | 200 | 90 | 70 | 95 | 95 | 99 | 88 |
| 10.6 | 200 | 90 | 62 | 95 | 95 | 100 | 93 |

TABLE 9

Synergistic Activity of Foliar-Applied Compound A
Benzyl Ester and Benzobicyclon Herbicidal Compositions
on Weed Control in a Rice Cropping System.

| Compound A | Benzo- | Visual Weed Control (%) - 22 DAA | | | |
|---|---|---|---|---|---|
| Benzyl Ester | bicyclon | ECHCG | | ECHCO | |
| gae/ha | gai/ha | Obs | Exp | Obs | Exp |
| 4.38 | 0 | 40 | — | 30 | — |
| 8.75 | 0 | 60 | — | 55 | — |
| 0 | 50 | 0 | — | 10 | — |
| 0 | 100 | 20 | — | 10 | — |
| 0 | 200 | 15 | — | 85 | — |
| 4.38 | 50 | 45 | 40 | 80 | 37 |
| 8.75 | 50 | 75 | 60 | 80 | 60 |
| 4.38 | 100 | 85 | 52 | 85 | 37 |
| 8.75 | 100 | 85 | 68 | 90 | 60 |
| 4.38 | 200 | 90 | 49 | 90 | 90 |
| 8.75 | 200 | 90 | 66 | 95 | 93 |

| Compound A | Benzo- | Visual Weed Control (%) - 22 DAA CYPIR | |
|---|---|---|---|
| Benzyl Ester | bicyclon | | |
| gae/ha | gai/ha | Obs | Exp |
| 4.38 | 0 | 10 | — |
| 8.75 | 0 | 65 | — |
| 0 | 100 | 0 | — |
| 0 | 200 | 0 | — |
| 4.38 | 100 | 30 | 10 |
| 8.75 | 100 | 95 | 65 |
| 4.38 | 200 | 50 | 10 |
| 8.75 | 200 | 100 | 65 |

| | | |
|---|---|---|
| BRAPP | *Brachiaria platyphylla* (Griseb.) Nash or *Urochloa platyphylla* (Nash) R. D. Webster | signalgrass, broadleaf |
| CYPES | *Cyperus esculentus* L. | nutsedge, yellow |
| CYPIR | *Cyperus iria* L. | flatsedge, rice |
| DIGSA | *Digitaria sanguinalis* (L.) Scop. | crabgrass, large |
| ECHCG | *Echinochloa crusgalli* (L.) Beauv. | barnyardgrass |
| ECHCO | *Echinochloa colona* (L.) Link | junglerice |
| IPOHE | *Ipomoea hederacea* Jacq. | morningglory, ivyleaf |
| LEFCH | *Leptochloa chinensis* (L.) Nees | sprangletop, Chinese |
| SCPJU | *Schoenoplectus juncoides* (Roxb.) Palla | bulrush, Japanese | gae/ha = grams acid equivalent per hectare
gai/ha = grams active ingredient per hectare
Obs = observed value
Exp = expected value as calculated by Colby's equation
DAA = days after application Example II Evaluation of in-Water Applied Herbicidal Mixtures
for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 840 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29'C during the day and 26° C. during the night. Nutrients were added as Osmocote® (19:6:12, N:P:K+ minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (compound A) each formulated as an SC (suspension concentrate) and various herbicidal components alone and in combination. Forms of compound A were applied on an acid equivalent basis.

Forms of compound A (compound of formula I) tested include:

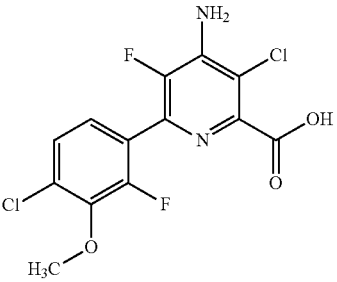

Compound A Acid

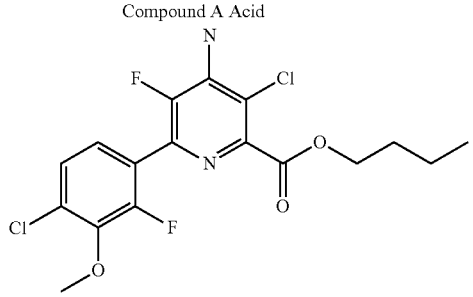

Compound A n-Butyl Ester

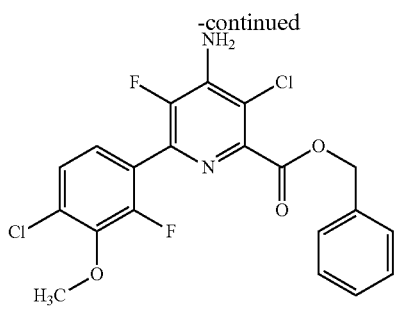

Compound A Benzyl Ester

Other herbicidal components were applied on an active ingredient basis and included 4-hydroxyphenyl pyruvate dioxygenase (HPPD)-inhibiting herbicides mesotrione formulated as Callisto®, sulcotrione formulated as Mikado®, pyrazolynate formulated as Sunbird® 10% GR, and benzobicyclon formulated as Benzobicyclon 3.5% or technical material.

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 10-19.

TABLE 10

Synergistic Activity of In-Water Applications of Compound A Acid and Mesotrione Herbicidal Compositions on Weed Control in a Rice Cropping System.

| Compound A Acid | Mesotrione | Visual Weed Control (%) - 20 DAA ECHCG | |
|---|---|---|---|
| gae/ha | gai/ha | Obs | Exp |
| 8.75 | 0 | 0 | — |
| 17.5 | 0 | 35 | — |
| 35 | 0 | 55 | — |
| 0 | 35 | 10 | — |
| 0 | 70 | 25 | — |
| 8.75 | 35 | 30 | 10 |
| 17.5 | 35 | 50 | 42 |
| 35 | 35 | 99 | 60 |
| 8.75 | 70 | 40 | 25 |
| 17.5 | 70 | 45 | 51 |
| 35 | 70 | 75 | 66 |

| Compound A Acid | Mesotrione | Visual Weed Control (%) - 20 DAA ECHOR | |
|---|---|---|---|
| gae/ha | gaiha | Obs | Exp |
| 42.4 | 0 | 18 | — |
| 84.8 | 0 | 33 | — |
| 0 | 140 | 80 | — |
| 42.4 | 140 | 93 | 84 |
| 84.8 | 140 | 100 | 87 |

TABLE 11

Synergistic Activity of In-Water Applications of Compound A n-Butyl Ester and Mesotrione Herbicidal Compositions on Weed Control in a Rice Cropping System.

| Compound A n-Butyl Ester | Mesotrione | Visual Weed Control (%) -20 DAA ECHOR | |
|---|---|---|---|
| gae/ha | gaiha | Obs | Exp |
| 35 | 0 | 35 | — |
| 70 | 0 | 40 | — |
| 0 | 140 | 80 | — |
| 35 | 140 | 100 | 87 |
| 70 | 140 | 100 | 88 |

TABLE 12

Synergistic Activity of In-Water Applications of Compound A Benzyl Ester and Mesotrione Herbicidal Compositions on Weed Control in a Rice Cropping System.

| Compound A Benzyl Ester | Mesotrione | Visual Weed Control (%) - 21 DAA FIMMI | |
|---|---|---|---|
| gae/ha | gai/ha | Obs | Exp |
| 8 | 0 | 15 | — |
| 16 | 0 | 65 | — |
| 0 | 35 | 78 | — |
| 8 | 35 | 100 | 81 |
| 16 | 35 | 100 | 92 |

TABLE 12-continued

Synergistic Activity of In-Water Applications of Compound A Benzyl Ester and Mesotrione Herbicidal Compositions on Weed Control in a Rice Cropping System.

| Compound A Benzyl Ester | Mesotrione | Visual Weed Control (%) - 21 DAA SCPMA | |
|---|---|---|---|
| gae/ha | gai/ha | Obs | Exp |
| 8 | 0 | 0 | — |
| 16 | 0 | 0 | — |
| 32 | 0 | 0 | — |
| 0 | 35 | 80 | — |
| 8 | 35 | 100 | 80 |
| 16 | 35 | 100 | 80 |
| 32 | 35 | 100 | 80 |

TABLE 13

Synergistic Activity of In-Water Applications of Compound A Acid and Sulcotrione Herbicidal Compositions on Control of Weeds Common to Rice Cropping Systems.

| Compound A Acid | Sulcotrione | Visual Weed Control (%) - 20 DAA ECHCG | |
|---|---|---|---|
| gae/ha | gai/ha | Obs | Exp |
| 8.75 | 0 | 40 | — |
| 17.5 | 0 | 30 | — |
| 0 | 22.5 | 0 | — |
| 8.75 | 22.5 | 90 | 40 |
| 17.5 | 22.5 | 100 | 30 |

Synergistic Activity of In-Water Applications of Compound A Benzyl Ester and Sulcotrione Herbicidal Compositions on Control of Weeds Common to Rice Cropping Systems.

| Compound A Benzyl Ester | Sulcotrione | Visual Weed Control (%) - 20 DAA ECHOR | |
|---|---|---|---|
| gae/ha | gai/ha | Obs | Exp |
| 4.38 | 0 | 10 | — |
| 8.75 | 0 | 20 | — |
| 17.5 | 0 | 30 | — |
| 0 | 22.5 | 10 | — |
| 4.38 | 22.5 | 30 | 19 |
| 8.75 | 22.5 | 45 | 28 |
| 17.5 | 22.5 | 55 | 37 |

TABLE 14

Synergistic Activity of In-Water Applications of Compound A Acid and Pyrazolynate Herbicidal Compositions on Weed Control in a Rice Cropping System.

| Compound A Acid | Pyrazolynate | Visual Weed Control (%) - 21 DAA | | | | | |
|---|---|---|---|---|---|---|---|
| | | ECHCG | | ECHCO | | LEFCH | |
| gae/ha | gai/ha | Obs | Exp | Obs | Exp | Obs | Exp |
| 8.75 | 0 | 20 | — | 0 | — | 0 | — |
| 17.5 | 0 | 30 | — | 20 | — | 0 | — |
| 0 | 37.5 | 0 | — | 0 | — | 0 | — |
| 0 | 75 | 0 | — | 0 | — | 50 | — |
| 8.75 | 37.5 | 50 | 20 | 0 | 0 | 20 | 0 |
| 17.5 | 37.5 | 95 | 30 | 35 | 20 | 100 | 0 |
| 8.75 | 75 | 25 | 20 | 25 | 0 | 100 | 50 |
| 17.5 | 75 | 45 | 30 | 40 | 20 | 100 | 50 |

TABLE 14-continued

Synergistic Activity of In-Water Applications of Compound A Acid and Pyrazolynate Herbicidal Compositions on Weed Control in a Rice Cropping System.

| Compound A Acid | Pyrazolynate | Visual Weed Control (%) - 21 DAA FIMMI | |
|---|---|---|---|
| gae/ha | gai/ha | Obs | Exp |
| 17.5 | 0 | 85 | — |
| 35 | 0 | 85 | — |
| 0 | 37.5 | 0 | — |
| 0 | 75 | 0 | — |
| 17.5 | 37.5 | 100 | 85 |
| 35 | 37.5 | 100 | 85 |
| 17.5 | 75 | 90 | 85 |
| 35 | 75 | 100 | 85 |

| Compound A Acid | Pyrazolynate | Visual Weed Control (%) - 21 DAA SCPMA | |
|---|---|---|---|
| gae/ha | gai/ha | Obs | Exp |
| 8.75 | 0 | 0 | — |
| 17.5 | 0 | 0 | — |
| 35 | 0 | 0 | — |
| 0 | 37.5 | 0 | — |
| 8.75 | 37.5 | 30 | 0 |
| 17.5 | 37.5 | 30 | 0 |
| 35 | 37.5 | 100 | 0 |

| Compound A Benzyl Ester | Pyrazolynate | Visual Weed Control (%) - 21 DAA ECHOR | |
|---|---|---|---|
| gae/ha | gai/ha | Obs | Exp |
| 96 | 0 | 80 | — |
| 0 | 37.5 | 0 | — |
| 0 | 75 | 8 | — |
| 0 | 150 | 13 | — |
| 96 | 37.5 | 95 | 80 |
| 96 | 75 | 95 | 81 |
| 96 | 150 | 100 | 82 |

TABLE 15

Synergistic Activity of In-Water Applications of Compound A Benzyl Ester and Pyrazolynate Herbicidal Compositions on Weed Control in a Rice Cropping System.

| Compound A Benzyl Ester | Pyrazolynate | Visual Weed Control (%) - 21 DAA LEFCH | |
|---|---|---|---|
| gae/ha | gai/ha | Obs | Exp |
| 4.38 | 0 | 15 | — |
| 8.75 | 0 | 15 | — |
| 0 | 37.5 | 0 | — |
| 0 | 75 | 50 | — |
| 4.38 | 37.5 | 100 | 15 |
| 8.75 | 37.5 | 100 | 15 |
| 4.38 | 75 | 100 | 58 |
| 8.75 | 75 | 100 | 58 |

| Compound A Benzyl Ester | Pyrazolynate | Visual Weed Control (%) - 21 DAA CYPRO | |
|---|---|---|---|
| gae/ha | gai/ha | Obs | Exp |
| 17.5 | 0 | 10 | — |
| 0 | 37.5 | 0 | — |
| 0 | 75 | 0 | — |
| 17.5 | 37.5 | 60 | 10 |
| 17.5 | 75 | 50 | 10 |

TABLE 15-continued

Synergistic Activity of In-Water Applications of Compound A Benzyl Ester and Pyrazolynate Herbicidal Compositions on Weed Control in a Rice Cropping System.

| Compound A Benzyl Ester | Pyrazolynate | Visual Weed Control (%) - 21 DAA SCPJU | |
|---|---|---|---|
| gae/ha | gai/ha | Obs | Exp |
| 4.38 | 0 | 70 | — |
| 0 | 37.5 | 0 | — |
| 0 | 75 | 0 | — |
| 4.38 | 37.5 | 99 | 70 |
| 4.38 | 75 | 99 | 70 |

TABLE 16

Synergistic Activity of In-Water Applications of Compound A Acid and Benzobicyclon (3.5%) Herbicidal Compositions on Weed Control in a Rice Cropping System.

| Compound A Acid | Benzobicyclon | Visual Weed Control (%) - 22 DAA CYPRO | |
|---|---|---|---|
| gae/ha | gai/ha | Obs | Exp |
| 10.6 | 0 | 0 | — |
| 21.2 | 0 | 40 | — |
| 0 | 100 | 30 | — |
| 0 | 200 | 45 | — |
| 10.6 | 100 | 30 | 30 |
| 21.2 | 100 | 95 | 58 |
| 10.6 | 200 | 30 | 45 |
| 21.2 | 200 | 99 | 67 |

TABLE 17

Synergistic Activity of In-Water Applications of Compound A Acid and Benzobicyclon (technical) Herbicidal Compositions on Weed Control in a Rice Cropping System.

| Compound | | Visual Weed Control (%) - 22 DAA | | | |
|---|---|---|---|---|---|
| A Acid | Benzobicyclon | ECHOR | | CYPRO | |
| gae/ha | gai/ha | Obs | Exp | Obs | Exp |
| 21.2 | 0 | 20 | — | 60 | — |
| 42.4 | 0 | 40 | — | 90 | — |
| 0 | 50 | 50 | — | 10 | — |
| 21.2 | 50 | 50 | 60 | 90 | 64 |
| 42.4 | 50 | 100 | 70 | 95 | 91 |

TABLE 18

Synergistic Activity of In-Water Applications of Compound A Benzyl Ester and Benzobicyclon (3.5%) Herbicidal Compositions on Weed Control in a Rice Cropping System.

| Compound A Benzyl Ester | Benzobicyclon | Visual Weed Control (%) - 22 DAA ECHCG | |
|---|---|---|---|
| gae/ha | gai/ha | Obs | Exp |
| 8.75 | 0 | 45 | — |
| 17.5 | 0 | 90 | — |
| 0 | 100 | 30 | — |
| 0 | 200 | 45 | — |
| 8.75 | 100 | 80 | 62 |
| 17.5 | 100 | 100 | 93 |
| 8.75 | 200 | 100 | 70 |
| 17.5 | 200 | 60 | 95 |

| Compound A Benzyl Ester | Benzobicyclon | Visual Weed Control (%) - 21 DAA SCPMA | |
|---|---|---|---|
| gae/ha | gai/ha | Obs | Exp |
| 48 | 0 | 0 | — |
| 96 | 0 | 0 | — |
| 0 | 100 | 70 | — |
| 0 | 200 | 93 | — |
| 48 | 100 | 100 | 70 |
| 96 | 100 | 100 | 70 |
| 48 | 200 | 99 | 93 |
| 96 | 200 | 100 | 93 |

TABLE 19

Synergistic Activity of In-Water Applications of Compound A Benzyl Ester and Benzobicyclon (technical) Herbicidal Compositions on Weed Control in a Rice Cropping System.

| Compound A Benzyl Ester | Benzo-bicyclon | Visual Weed Control (%) - 21 DAA | | | |
|---|---|---|---|---|---|
| | | ECHOR | | SCPMA | |
| gae/ha | gae/ha | Obs | Exp | Obs | Exp |
| 4.38 | 0 | 25 | — | 0 | — |
| 8.75 | 0 | 25 | — | 0 | — |
| 17.5 | 0 | 60 | — | 0 | — |
| 0 | 100 | 30 | — | 80 | — |
| 4.38 | 100 | 50 | 48 | 100 | 80 |
| 8.75 | 100 | 50 | 48 | 90 | 80 |
| 17.5 | 100 | 100 | 72 | 85 | 80 |

TABLE 19-continued

Synergistic Activity of In-Water Applications of Compound A Benzyl Ester and Benzobicyclon (technical) Herbicidal Compositions on Weed Control in a Rice Cropping System.

| Compound A Benzyl Ester | Benzo-bicyclon | Visual Weed Control (%) - 22 DAA ECHOR | |
|---|---|---|---|
| gae/ha | gai/ha | Obs | Exp |
| 8.75 | 0 | 40 | |
| 17.5 | 0 | 95 | |
| 0 | 50 | 50 | |
| 8.75 | 50 | 100 | 70 |
| 17.5 | 50 | 100 | 98 |

| | | |
|---|---|---|
| CYPRO | *Cyperus rotundus* L. | nutsedge, purple |
| ECHCG | *Echinochloa crusgalli* (L.) Beauv. | barnyardgrass |
| ECHOR | *Echinochloa oryzoides* (Ard.) Fritsch | watergrass, early |
| FIMMI | *Fimbristylis miliacea* (L.) Vahl | fringerush, globe |
| LEFCH | *Leptochloa chinensis* (L.) Nees | sprangletop, Chinese |
| SCPJU | *Schoenoplectus juncoides* (Roxb.) Palla | bulrush, Japanese |
| SCPMA | *Bolboschoenus maritimus* (L.) Palla or *Schoenoplectus maritimus* (L.) Lye | clubrush, sea | gae/ha = grams acid equivalent per hectare
gai/ha = grams active ingredient per hectare
Obs = observed value
Exp = expected value as calculated by Colby's equation
DAA = days after application Example III Evaluation of Pre-emergence Soil-Applied Herbicidal Mixtures for Weed Control Seeds or nutlets of the desired test plant species were planted in a soil matrix prepared by mixing a loam soil (32 percent silt, 23 percent clay, and 45 percent sand, with a pH of about 6.5 and an organic matter content of about 1.9 percent) and calcareous grit in an 80 to 20 ratio. The soil matrix was contained in plastic pots with a volume of 1 quart and a surface area of 83.6 square centimeters ($cm^2$).

Treatments consisted of the benzyl ester of 4-amino-3-chloro-5-fluoro-6-(4-chloro-2-fluoro-3-methoxy-phenyl) pyridine-2-carboxylic acid (compound A) formulated as an SC (suspension concentrate) and various herbicidal components alone and in combination. Forms of compound A were applied on an acid equivalent basis.
Forms of compound A (compound of formula I) tested include:

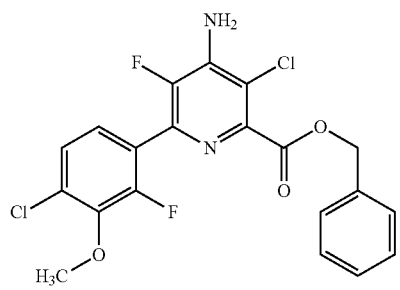

Compound A Benzyl Ester

Other herbicidal components were applied on an acid equivalent or active ingredient basis and included the 4-hydroxyphenyl pyruvate dioxygenase (HPPD)-inhibiting herbicide, isoxaflutole, formulated as Balance Pro®.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrate (COC) to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) COC so that the final spray solutions contained 1.25% (v/v) COC.

For treatments comprised of technical compounds, weighed amounts can be placed individually in 25 mL glass vials and dissolved in a volume of 97:3 (v/v) acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) COC so that the final spray solutions contain 1.25% (v/v) COC. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 (v/v) acetone/DMSO to obtain 12× stock solutions, and measured amounts of the formulated compounds can be placed individually in 25 mL glass vials and diluted in a volume of 1.5% (v/v) COC or water to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) COC so that the final spray solutions contain 1.25% (v/v) COC. As required, additional water and/or 97:3 (v/v) acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Spray solutions were applied to the soil with an overhead Mandel track sprayer equipped with a 8002E nozzles calibrated to deliver 187 L/ha over an application area of 0.503 m² at a spray height of 18 inches (46 cm) above average pot height. Control pots were sprayed in the same manner with the solvent blank.

The treated and control pots were placed in a greenhouse and top watered as needed. When required to ensure good germination and healthy plants, a fungicide treatment and/or other chemical or physical treatment was applied. The pots were maintained in a greenhouse with an approximate 14 hr photoperiod which was maintained at about 29° C. during the day and 26° C. during the night. Nutrients (Peters® Excel 15-5-15 5-Ca 2-Mg) were applied in the irrigation solution as needed and water was added on a regular basis. Supplemental lighting was provided with overhead metal halide 1000-Watt lamps as necessary. After approximately 4 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 20.

TABLE 20

Synergistic Activity of Soil-applied, Pre-emergence Applications of Compound A Benzyl Ester and Isoxaflutole Herbicidal Compositions on Weed Control

| Compound A | | Visual Weed Control (%) - 32 DAA | | | |
| Benzyl Ester | Isoxaflutole | IPOHE | | XANST | |
| gae/ha | gai/ha | Obs | Exp | Obs | Exp |
| 8 | 0 | 5 | — | 33 | — |
| 16 | 0 | 10 | — | 35 | — |
| 32 | 0 | 10 | — | 65 | — |
| 0 | 35 | 43 | — | 75 | — |
| 8 | 35 | 58 | 45 | 80 | 83 |
| 16 | 35 | 53 | 48 | 95 | 84 |
| 32 | 35 | 75 | 48 | 100 | 91 |

TABLE 20-continued

Synergistic Activity of Soil-applied, Pre-emergence Applications of Compound A Benzyl Ester and Isoxaflutole Herbicidal Compositions on Weed Control

| Compound A Benzyl Ester | Isoxaflutole | Visual Weed Control (%) - 32 DAA SETVI | |
| | | Obs | Exp |
| gae/ha | gai/ha | | |
| 16 | 0 | 0 | — |
| 32 | 0 | 13 | — |
| 0 | 35 | 50 | — |
| 0 | 70 | 93 | — |
| 16 | 35 | 53 | 50 |
| 32 | 35 | 70 | 56 |
| 16 | 70 | 100 | 93 |
| 32 | 70 | 100 | 93 |

IPOHE  *Ipomoea hederacea* (L.) Jacq.  morningglory, ivyleaf
SETVI  *Setaria viridis* (L.) Beauv.  foxtail, green
XANST  *Xanthium strumarium* L.  cocklebur, common
gae/ha = grams acid equivalent per hectare
gai/ha = grams active ingredient per hectare
Obs = observed value
Exp = expected value as calculated by Colby's equation
DAA = days after application

What is claimed is:

1. A herbicidal composition comprising a herbicidally effective amount of (a) a compound of the formula (I):

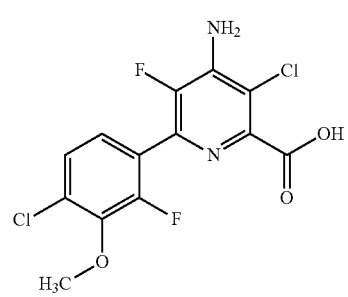

or an alkyl or benzyl ester, or an agriculturally acceptable salt of formula (I); and
(b) an HPPD inhibitor selected from benzobicyclon, benzofenap, isoxaflutole, mesotrione, pyrazolynate, sulcotrione or tefuryltrione or agriculturally acceptable salt or ester thereof, wherein (a) and (b) are present in the composition in a ratio such that the composition exhibits herbicidal synergy.

2. The composition of claim 1, wherein (a) is a $C_{1-4}$ alkyl or benzyl ester of the compound of formula (I).

3. The composition of claim 2, wherein (a) is a n-butyl or benzyl ester of the compound of formula (I).

4. The composition of claim 1, wherein (a) is the carboxylic acid of the compound of formula (I).

5. The composition of claim 1, further comprising a herbicide safener, adjunct and/or carrier.

6. The composition of claim 1, wherein the weight ratio of the compound of formula (I) or agriculturally acceptable salt or ester thereof to benzobicyclon or agriculturally acceptable salt or ester thereof is from about 1:150 to about 6:1.

7. The composition of claim 1, wherein the weight ratio of the compound of formula (I) or agriculturally acceptable salt or ester thereof to benzofenap or agriculturally acceptable salt or ester thereof is from about 1:600 to about 3:1.

8. The composition of claim 1, wherein the weight ratio of the compound of formula (I) or agriculturally acceptable salt or ester thereof to isoxaflutole or agriculturally acceptable salt or ester thereof is from about 1:70 to about 2:1.

9. The composition of claim 1, wherein the weight ratio of the compound of formula (I) or agriculturally acceptable salt or ester thereof to mesotrione or agriculturally acceptable salt or ester thereof is from about 1:115 to about 17:1.

10. The composition of claim 1, wherein the weight ratio of the compound of formula (I) or agriculturally acceptable salt or ester thereof to pyrazolynate or agriculturally acceptable salt or ester thereof is from about 1:229 to about 2:1.

11. The composition of claim 1, wherein the weight ratio of the compound of formula (I) or agriculturally acceptable salt or ester thereof to sulcotrione or agriculturally acceptable salt or ester thereof is from about 1:300 to about 13:1.

12. The composition of claim 1, wherein the weight ratio of the compound of formula (I) or agriculturally acceptable salt or ester thereof to tefuryltrione or agriculturally acceptable salt or ester thereof is from about 1:300 to about 6:1.

13. A method of controlling undesirable vegetation, comprising the steps of:
contacting a plant, wherein the plant is undesirable vegetation, or the locus thereof, soil or water, wherein the soil or the water allows for the growth of the undesirable vegetation, with a herbicidally effective amount of a combination comprising (a) a compound of the formula (I):

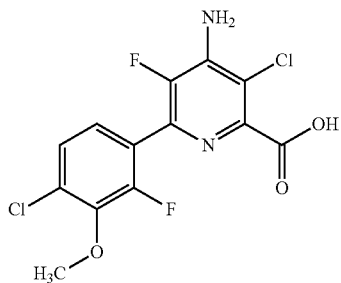

or an alkyl or benzylester, or an agriculturally acceptable salt of formula (I) and (b) an HPPD inhibitor selected from benzobicyclon, benzofenap, isoxaflutole, mesotrione, pyrazolynate, sulcotrione or tefuryltrione or agriculturally acceptable salt or ester thereof, wherein (a) and (b) are present in the combination in a ratio such that the combination exhibits herbicidal synergy; wherein the undesirable vegetation is controlled in direct-seeded, water-seeded and transplanted rice, cereals, wheat, barley, oats, rye, sorghum, corn, sugarcane, sunflower, oilseed rape, canola, sugar beet, soybean, cotton or pineapple crop.

14. The method of claim 13, wherein the water is part of a flooded rice paddy.

15. The method of claim 13, wherein the (a) and (b) are applied pre-emergently and/or post-emergently to the undesirable vegetation in the crop.

16. The method of claim 13, wherein the undesirable vegetation is at least partially controlled by at least one of the following agents: glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitor-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

17. The method of claim 13, wherein the undesirable vegetation comprises a herbicide resistant or tolerant plant.

18. The method of claim 13, wherein the resistant or tolerant plant is resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *